US011035861B2

(12) United States Patent
Yerramilli et al.

(10) Patent No.: US 11,035,861 B2
(45) Date of Patent: Jun. 15, 2021

(54) METHODS FOR DETECTING RENAL DISEASE

(71) Applicant: IDEXX Laboratories, Inc., Westbrook, ME (US)

(72) Inventors: Mahalakshmi Yerramilli, Falmouth, ME (US); Murthy V S N Yerramilli, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 64 days.

(21) Appl. No.: 15/061,327

(22) Filed: Mar. 4, 2016

(65) Prior Publication Data

US 2016/0187348 A1 Jun. 30, 2016

Related U.S. Application Data

(63) Continuation of application No. PCT/US2014/054278, filed on Sep. 5, 2014.

(60) Provisional application No. 61/874,011, filed on Sep. 5, 2013.

(51) Int. Cl.
*G01N 33/68* (2006.01)
*G01N 33/70* (2006.01)

(52) U.S. Cl.
CPC ......... *G01N 33/6812* (2013.01); *G01N 33/70* (2013.01); *G01N 2800/347* (2013.01); *G01N 2800/52* (2013.01); *Y02A 90/10* (2018.01)

(58) Field of Classification Search
CPC ......... G01N 2800/347; G01N 2800/52; G01N 33/6812; G01N 33/70; G01N 2800/60; Y02A 90/24
See application file for complete search history.

(56) References Cited

U.S. PATENT DOCUMENTS

| | | | |
|---|---|---|---|
| 4,485,177 A | 11/1984 | Siedel et al. | |
| 4,578,361 A | 3/1986 | Winfried et al. | |
| 4,818,703 A | 4/1989 | Pizzolante | |
| 5,318,680 A | 6/1994 | Fishman et al. | |
| 5,726,010 A | 3/1998 | Clark | |
| 6,358,699 B1 | 3/2002 | Balint et al. | |
| 6,455,288 B1 | 9/2002 | Jakobovitis et al. | |
| 6,699,673 B2 | 3/2004 | Aletta | |
| 6,720,188 B2 | 4/2004 | Kaddurah-Daouk et al. | |
| 6,736,957 B1 | 5/2004 | Forrow et al. | |
| 7,611,844 B2 | 11/2009 | Lin et al. | |
| 8,481,690 B2 | 7/2013 | Murthy et al. | |
| 9,091,684 B2 | 7/2015 | Yerramilli et al. | |
| 9,891,223 B2 | 2/2018 | Beauliu et al. | |
| 2004/0214252 A1 | 10/2004 | Lin et al. | |
| 2004/0242723 A1 | 12/2004 | Jin et al. | |
| 2005/0148029 A1* | 7/2005 | Buechler | C12Q 1/6883 435/7.1 |
| 2005/0266574 A1 | 12/2005 | Kosaka | |
| 2006/0094122 A1 | 5/2006 | Boeger et al. | |
| 2006/0201805 A1 | 9/2006 | Forrow et al. | |
| 2010/0035274 A1* | 2/2010 | Murthy | C07C 279/12 435/7.1 |
| 2010/0129828 A1* | 5/2010 | Beaulieu | G01N 33/57419 435/7.1 |
| 2012/0129265 A1 | 5/2012 | Lundin et al. | |
| 2014/0038203 A1* | 2/2014 | Arthur | G01N 33/6893 435/7.4 |

FOREIGN PATENT DOCUMENTS

| | | |
|---|---|---|
| CN | 101587118 | 11/2009 |
| CN | 101598727 | 12/2009 |
| CN | 101865911 | 10/2010 |
| EP | 1666884 | 6/2006 |
| EP | 2612147 B1 | 5/2012 |
| JP | S5853761 | 3/1983 |
| JP | 2008525110 A | 7/2008 |
| JP | 2010533851 A | 10/2010 |
| JP | 2011506922 | 3/2011 |
| JP | 2012112785 A | 6/2012 |
| JP | 2012529015 | 11/2012 |
| WO | WO9634271 | 10/1996 |
| WO | 1998/49199 | 11/1998 |
| WO | WO0204950 | 1/2002 |
| WO | 2002/014873 | 2/2002 |

(Continued)

OTHER PUBLICATIONS

Nabity et al., "Correlation of symmetric dimethylarginine with glomerular filtration rate in dogs with chronic progressive renal disease," J. Vet. Intern. Med., May 2013, 27(3)133.
Kielstein et al., "SDMA is an early marker of change in GFR after living-related kidney donation," Nephrology Dialysis Transplantation, Jul. 2011, pp. 324-328, vol. 26, No. 1.
Sopio et al., "Reaction of 3-deoxypentosulose with N-methyl- and N, N-dimethylguanidine as model reagents for protein-bound arginine and for creatine," Z. Lebensm. Unters Forsch. A., 1995, pp. 381-386, vol. 201.
Stuhlinger et al., "Relationship Between Insulin Resistance and an Endogenous Nitric Oxide Synthase Inhibitor," J. Am. Med. Assoc., 2002, pp. 1420-1426, vol. 287, No. 1.
Szurdoki et al., "Important Factors in Hapten Design and Enzyme-Linked Immunosorbent Assay Development," Immunoanalysis of Agrochemicals, ACS Symposium Series, American Chemical Society, 1995, pp. 39-63, Chapter 4, vol. 586.

(Continued)

*Primary Examiner* — Galina M. Yakovleva
(74) *Attorney, Agent, or Firm* — McDonnell Boehnen Hulbert & Berghoff LLP

(57) ABSTRACT

The disclosure is directed to methods and apparatus for the determination, diagnosis, progression and prognosis of kidney disease and mortality associated with kidney disease. The disclosure includes methods for determining renal function, in particular estimating glomerular filtration rate (GFR), in an animal. GFR can be useful in the diagnosis and treatment of kidney disease or dysfunction. In various aspects, the disclosure is directed to the use of free symmetrical dimethylarginine (SDMA) and creatinine in blood samples from animals, in particular cats and dogs, to determine glomerular filtration rate and kidney disease.

10 Claims, 20 Drawing Sheets

(56) References Cited

FOREIGN PATENT DOCUMENTS

| WO | 2004/046314 | 6/2004 |
|---|---|---|
| WO | 2006/078813 | 7/2006 |
| WO | 2007/074864 | 7/2007 |
| WO | WO2009071904 | 6/2009 |
| WO | 2010/017089 | 2/2010 |
| WO | WO2010139341 | 12/2010 |
| WO | 2015/035155 | 3/2015 |

OTHER PUBLICATIONS

Takahashi, Kenji, "The Reaction of Phenylglyoxal with Arginine Residues in Proteins," J. Biol. Chem., Dec. 10, 1968, pp. 6171-6179, vol. 243, No. 23.

Teerlink et al., "Determination of Arginine, Asymmetric Dimethylarginine, and Symmetric Dimethylarginine in Human Plasma and Other Biological Samples by High-Performance Liquid Chromatography," Anal. Biochem., 2002, pp. 131-137, vol. 303.

Upstate cell signaling solutions, "Certificate of Analysis for Anti-dimethyl-Arginine, symmetric (SYM10)," rabbit polyclonal IgG; downloaded May 24, 2011 from www.millipore.com, 2 pages.

Upstate cell signaling solutions, "Certificate of Analysis for Anti-dimethyl-Arginine, symmetric (SYM11)," rabbit polyclonal IgG; downloaded May 24, 2011 from www.millipore.com, 2 pages.

Vanholder et al., Review on uremic toxins: Classification, concentration, and interindividual variability, Kidney International, May 1, 2003, pp. 1934-1943, vol. 63.

Vishwanathan et al., "Determination of arginine and methylated arginines in human plasma by liquid chromatography-tandem mass spectrometry," Journal of Chromatography B, 2000, pp. 157-166, vol. 748.

"ADMA—ELISA, Enzyme Immunoassay for the quantitative Determination of Endogenous Asymmetric Dimethylarginine (ADMA) in Serum or Plasma (Instruction for use)," Diagnostika GMBH, Apr. 2007, 16 pages.

Baburaj, K. et al., "HOCGO and DMACGO. Two coumarin derived alpha-dicarbonyls suitable as pH and polarity sensitive fluorescent reporters for proteins that can be targeted at reactive arginines," Biochim. Biophys. Acta, 1994, pp. 253-265, vol. 1199.

Bedford et al., "Arginine Methylation: An Emerging Regulator of Protein Function," Mol. Cell, 2005, pp. 263-272, vol. 18.

Biovendor Research and Diagnostic Products: "Enzyme Immunoassay for the Quantitative Determination of Endogenous Symmetric Dimethylarginine (SDMA) on Serum or Plasma", SDMA ELISA, Instructions for use, 2008, 13 pages.

Blackwell et al., "Biological variation of asymmetric dimethylarginine and related arginine metabolites and analytical performance goals for their measurement in human plasma," European Journal of Clinical Investigation, 2007, pp. 364-371, vol. 37.

Bode-Böger et al., "Symmetrical Dimethylarginine: A New Combined Parameter for Renal Function and Extent of Coronary Artery Disease," Journal of the American Society of Nephrology, 2006, pp. 1128-1134, vol. 17.

Bode-Böger, S.M. et al., "Elevated L-Arginine/Dimethylarginine Ratio Contributes to Enhanced Systemic NO Production by Dietary L-Arginine in Hypercholesterolemic Rabbits," Biochem. Biophys. Res. Commun., 1996, pp. 598-603, vol. 219.

Böger, Rainer, "Asymmetric dimethylarginine (ADMA): A novel risk marker in cardiovascular medicine and beyond," Annals of Medicine, 2006, pp. 126-136, vol. 38.

Boisvert et al., A Proteomic Analysis of Arginine-Methylated Protein Complexes, Molecular & Cellular Proteomics, 2003, pp. 1319-1330, vol. 2, No. 12.

Boisvert, Francois-Michel, "A Role for Arginine Methylation in DNA Repair," Dissertation abstracts International, 2005, 234 pages.

Boisvert et al., "Symmetrical dimethylarginine methylation is required for the localization of SNM in Cajal bodies and pre-mRNA splicing", J. Cell Biol, 2002, vol. 159, No. 6, pp. 957-969, vol. 59, No.6.

Brahms et al., "The C-terminal RG Dipeptide Repeats of the Spliceosomal Sm Proteins D1 and D3 contain Symmetrical Dimethylarginines, Which Form a Major B-cell epitope for Anti-Sm Autoantibodies," The Journal of Biological Chemistry, 2000, pp. 17122-17129, vol. 275, No. 22.

Chen et al., "Determination of NG, NG-dimethylarginine in human plasma by high-performance liquid chromatography," Journal of Chromatography B, 1997, pp. 467-471, vol. 692.

Cooper et al. "Cyclic Forms of the alpha-Keto Acid Analogs of Arginine, Citrulline, Homoarginine, and Homocitrulline," J. Biol. Chem., Aug. 10, 1978, pp. 5407-5410, vol. 253, No. 15.

Dobashi et al., "An automated analyzer for methylated arginines in rat plasma by high-performance liquid chromatography with post-column fluorescence reaction," Analyst, 2002, pp. 54-59, vol. 127.

Duerksen, P.J. et al., Immobilization of Proteins Via Arginine Residues, Anal. Biochem., 1987, pp. 444-454, vol. 160.

Duncan et al., "A New Reagent Which may be Used to Introduce Sulfhydryl Groups into Proteins, and Its use in the Preparation of Conjugates for Immunoassay," Analytical Biochemistry, 1983, pp. 68-73, vol. 132.

Finco, et al., "Relationship between plasma creatinine concentration and glomerular filtration rate in dogs," Journal of Veterinary Pharmacology and Therapeutics, 1995, pp. 418-421, vol. 18.

Fleck et al., "Serum concentrations of asymmetric (ADMA) and symmetric (SDMA) dimethylarginine in renal failure patients," Kidney International, 2001, pp. 14-18, vol. 59, No. 78.

Fliser et al., "Asymmetric Dimethylarginine and Progression of Chronic Kidney Disease: The Mild to Moderate Kidney Disease Study," Journal of the American Society of Nephrology, 2005, pp. 2456-2461, vol. 16.

Goodrow et al., "Strategies for Immunoassay Hapten Design," Immunoanalysis of Agrochemicals, ACS Symposium Series, American Chemical Society, 1995, pp. 119-139, Chapter 9, vol. 586.

Greene, T.W. et al., "Chapter 5—Protection for the Carboxyl Group," Protective Groupsin Organic Synthesis, 3rd Edition, 1999, pp. 369-453.

Greene, T.W. et al., "Chapter 6—Protection for the Thiol Group," Protective Groupsin Organic Synthesis, 3rd Edition, 1999, pp. 454-493.

Greene, T.W. et al., "Chapter 7—Protection for the Amino Group," Protective Groupsin Organic Synthesis, 3rd Edition, 1999, pp. 494-653.

Kielstein et al., "Symmetric dimethylarginine (SDMA) as endogenous marker of renal function—a meta-analysis," Nephrol Dialysis Transplantation, 2006, pp. 2446-2451, vol. 21.

Kitagawa et al., "Preparation and Characterization of Hetero-Bifunctional Cross-linking Reagents for Protein Modificiations," Chem. Pharm. Bull, 1981, pp. 1130-1135, vol. 29, No. 4.

Koch et al., "Regulation and Prognostic Relevance of Symmetric Dlmethylarginine Serum Concentrations in Critical Illness and Sepsis," Mediators of Inflammation, Jun. 27, 2013, pp. 1-8, vol. 2013.

Levey et al., "Glomerular filtration rate measurements in clinical trials. Modification of Diet in Renal Disease Study Group and the Diabetes Control and Complications Trial Research Group." Journal of the American Society of Nephrology , 1993, pp. 1159-1171, vol. 4, No. 5.

Liu et al., "New procedures for preparation and isolation of conjugates of proteins and a synthetic copolymer of D-amino acids and immunochemical characterization of such conjugates," Biochemistry, 1979, pp. 690-697, vol. 18, No. 4.

MacAllister et al., "Concentration of dimethyl-L-arginine in the plasma of patients with end-stage renal failure," Nephrology Dialysis Transplantation, Dec. 11, 1996, pp. 2449-2452, vol. 11.

Mahler et al., "Identification of a SmD3 epitope with a single symmetrical dimethylation of an arginine residue as a specific target of a subpopulation of anti-Sm antibodies," Arthritis Research & Therapy, 2004, pp. R19-R29, vol. 7, No. 1.

Midttun et al., "High-throughput, low-volume, multianalyte quantification of plasma metabolites related to one-carbon metabolism using HPLC-MS/MS," Analytical and Bioanalytical Chemistry, Dec. 13, 2012, pp. 2009-2017, vol. 405.

(56) References Cited

OTHER PUBLICATIONS

Moesgaard et al., "Effects of breed, gender, exercise and white-coat effect on markers of endothelial function in dogs," Research in Veterinary Science, 2007, pp. 409-418, vol. 82.

Nabity et al., "Day-to-Day Variation of the Urine Protein: Creatinine Ratio in Female Dogs with Stable Glomerular Proteinuria Caused by X-Linked Hereditary Nephropathy," J. Vet. Intern. Med., 2007, pp. 425-430, vol. 21.

Nijveldt et al., "Handling of asymmetrical dimethylarginine and symmetrical dimethylarginine by the rat kidney under basal conditions and during endotoxaemia," Nephrol Dial. Transplant, 2003, pp. 2542-2550, vol. 18.

Ogawa et al., "Metabolism of Ng, NG- and NG, N'G-Dimethylarginine in rats," Arch. Biochem. Biophys., Feb. 1, 1987, pp. 526-537, vol. 252, No. 2.

Palmer et al., "Reduction and Reoxidation of a Critical Disulfide Bond in the Rabbit Antibody Molecule," J. Biol. Chem., 1963, pp. 2393-2398, vol. 238, No. 7.

Perrone et al., "Utility of Radioisotopic Filtration Markers in Chronic Renal Insufficiency: Simultaneous Comparison of 125I-Iothalamate, 169Yb-DTPA, 99mTc-DTPA, and Inulin," Am. J. Kidney Disease, 1990, pp. 224-235, vol. 16, No. 3.

Peterson et al., "Using Hapten Design to Discover Therapeutic Monoclonal Antibodies for Treating Methamphetamine Abuse," The Journal of Pharmacology and Experimental Therapeutics, 2007, pp. 30-39, vol. 322, No. 1.

Pettersson et al., Determination of dimethylated arginines in human plasma by high-performance liquid chromatography, Journal of Chromatography B, 1997, pp. 257-262, vol. 692.

Pi et al., "Improved method for simultaneous determination of L-arginine and its mono- and dimethylated metabolites in biological samples by high-performance liquid chromatography," Journal of Chromatography B, 2000, pp. 199-203, vol. 742.

Pravetoni et al., "Structurally distinct nicotine immunogens elicit antibodies with non-overlapping specificities," Biochemical Pharmacology, 2012, pp. 543-550, vol. 83, No. 4.

Product Information List, DLD Diagnostika GmbH, retrieved online www.dld-diagnostika.de/produkt_en.php?id=52, Jan. 25, 2011, 2 pages.

Richard et al., "Arginine methylation regulates IL-2 gene expression: a role for protein arginine methyltransferase 5 (PRMT5)," Biochem J., 2005, pp. 379-386, vol. 388.

Schnabel et al., "Asymmetric Dimethylarginine and the Risk of Cardiovascular events and Death in Patients with Coronary Artery Disease—results from the AtheroGene Study," Circulation Research, 2005, pp. 1-7, vol. 97.

Schulze et al., "Determination of asymmetric dimethylarginine (ADMA) using a novel ELISA assay," Clin. Chem. Lab Med., 2004, pp. 1377-1383, vol. 42, No. 12.

Schulze et al., "Determination of a reference value for NG, NG-dimethyl-L-arginine in 500 subjects," European Journal of Clinical Investigation, 2005, pp. 622-626, vol. 35.

Schwarzenbolz, U. et al., "On the reaction of glyoxal with proteins," Zeitschrift für Lebensmitteluntersuchung und—Forschung A, 1997, pp. 121-124, vol. 205.

SDMA (human) ELISA kit, Enzo Life Sciences, Version 01: Dec. 8, 2009, 19 pages.

SDMA—ELISA, "Instructions for Use; Enzyme Immunoassay for the quantitative Determination of Endogenous Symmetric Dimethylarginine (SDMA) in Serum or Plasma," DLD Diagnostika GMBH, Feb. 2008, 16 pages.

Fleck, et al., "Serum concentrations of asymmetric (ADMA) and symmetric (SDMA) dimethylarginine in patients with chronic kidney diseases", Clinica Chimica Acta, 336:1-12 (2003).

Nabity et al., "Symmetric Dimethylarginine Assay Validation, Stability, and Evaluation as a Marker for the Early Detection of Chronic Kidney Disease in Dogs," J Vet Intern Med. 29(4):1036-44 (2015).

Stevens, et al., "Assessing Kidney Function—Measured and Estimated Glomerular Filtration Rate." NEJM, 354:23, 2473-2483 (2006).

Jepsen, RE. et al., "Plasma Asymmetric Dimethylarginine, Symmetric Dimethylarginine, L-Arginine, and NMitrite / Nitrate Concentrations in Cats with Chronic Kidney Disease and Hypertension." J Vet Intern Med, 22:317-324 (2008).

Immunodiagnostik AG—SDMA ELISA Kit for the Determination of SDMA in Human EDTA-Plasma and Serum—Instructions (2009), pp. 1-36.

Immunodiagnostik AG—SDMA ELISA Kit for the Determination of SDMA in Human EDTA-Plasma and Serum—Instructions (2012), pp. 17-30.

Chang Hwa Lee, "Estimation of GFR", The Korean Journal of Internal Medicine, 2012, vol. 83, pp. 455-457. • Concise summary of Chang Hwa Lee, "Estimation of GFR", from (1) a translation of an Office Action (dated Aug. 21, 2020) from the corresponding Korean patent application and (2) translation of the abstract via Google Translate.

* cited by examiner

METHODS FOR DETECTING RENAL DISEASE

RELATED APPLICATION

This is a Continuation Application of International Application Serial No. PCT/US2014/054278, filed Sep. 5, 2015, which claims the benefit of U.S. Provisional Patent Application No. 61/874,011 filed Sep. 5, 2013, each of which is incorporated by reference herein in its entirety.

FIELD

The disclosure generally relates to the determination of renal function. More particularly, the disclosure relates to methods for estimating glomerular filtration rate and diagnosing, prognosing and determining the progression of kidney disease.

RELATED ART

It is important to be able to measure renal function quickly and accurately. For example, the dosing of drugs must be adapted for patients with renal insufficiency. Thus, making an accurate assessment of renal function is a requirement in clinical medicine. However, the diagnosis of renal insufficiency is hindered by the lack of reliable markers of glomerular filtration rate (GFR) and/or available diagnostic tests. A widely used measurement of GFR is inulin clearance, but this test is cumbersome and expensive, which essentially reduces its utility in clinical practice. This also holds true for radioisotope clearance tests. Therefore, in clinical practice, serum creatinine is typically used to assess renal function. Uses of serum creatinine can, however, suffer from imprecision, as data can be subject to a relatively high degree of variability.

Accordingly, the inventors have identified a need in the art for methods of assessing renal function with increased precision.

SUMMARY

In one aspect, the disclosure is directed to a method for estimating glomerular filtration (GFR) rate in an animal subject. The method includes measuring the concentration of free SDMA in a blood sample from the subject, measuring the concentration of creatinine in a blood sample from the subject; and comparing a value resulting from an equation comprising the product of the concentration of creatinine and the concentration of free SDMA to one or more standard values that correlate to glomerular filtration rate in the animal subject.

In various exemplary embodiments of the method described herein, the equation comprises the inverse of the product of the concentration of creatinine and the concentration of free SDMA. Also, the concentration of creatinine and/or the concentration are free SDMA can be weighted in the calculation. The comparing step can be performed using a microprocessor. The method also includes determining renal function, kidney disease or kidney dysfunction by comparing the GFR in the subject to the GFR in one or more healthy subjects.

In yet another embodiment, the disclosure is directed to a method of diagnosing kidney disease or kidney dysfunction in an animal subject. The method includes measuring the concentration of free SDMA in serum from the subject; measuring the concentration of creatinine in serum from the subject; and comparing the product of a first weighted value based upon the concentration of creatinine and a second weighed value based upon the concentration free SDMA to one or more standard values that correlate to kidney disease or kidney dysfunction.

In particular exemplary embodiments, the product of a first weighted value based upon the concentration of creatinine and a second weighed value based upon the concentration free SDMA is represented by the formula $PROD=(CRE)^P \times (SDMA)^Q$ wherein PROD is the product, CRE is the concentration of creatinine, SDMA is the concentration of SDMA, P provides the weight to give to CRE in the formula, and Q provides the weight to give to SDMA in the formula. The one or more standard values may correlate to the inverse of the product.

A further aspect of the disclosure is directed to a method for calculating a value associated with the diagnoses of kidney disease or kidney dysfunction in an animal subject. The method includes executing machine readable instructions for calculating the product of a first weighted value based upon the concentration of creatinine in a blood sample from the subject and a second weighed value based upon the concentration of free SDMA in a blood sample from the subject.

In yet a further aspect, the disclosure is directed to a method of determining whether an individual has kidney disease. The method includes measuring concentrations of SDMA [SDMA] and creatinine [CRE] in a serum sample from the individual, calculating a ratio $[SDMA]/SDMA_{CUT}$, calculating a ratio $[CRE]/CRE_{CUT}$, calculating a Combination Value: $C=[SDMA]/SDMA_{CUT}+[CRE]/CRE_{CUT}$, and determining that the individual has kidney disease if C is greater than $C_{CUT}$, wherein, $SDMA_{CUT}$ is the cutoff value for SDMA, $CRE_{CUT}$ is the cutoff value for creatinine, and $C_{CUT}$ is the cutoff value for the Combination Value.

One method according to the disclosure includes determining whether an individual has kidney disease. The method includes measuring concentrations of SDMA [SDMA] and creatinine [CRE] in a serum sample from the individual, calculating a ratio $[SDMA]/SDMA_{CUT}$, calculating a ratio $[CRE]/CRE_{CUT}$, calculating a Combination Value: $C=[SDMA]/SDMA_{CUT}+[CRE]/CRE_{CUT}$, and determining that the individual has kidney disease if C is greater than $C_{CUT}$, wherein $SDMA_{CUT}$ is the cutoff value for SDMA, $CRE_{CUT}$ is the cutoff value for CRE and $C_{CUT}$ is the cutoff value for the Combination Value.

Still further, the disclosure is directed to a method for predicting early death in an animal subject, the method includes measuring the concentration of free SDMA in serum from the subject, measuring the concentration of creatinine in serum from the subject, calculating a ratio [SDMA]/[CRE], and determining that the individual will suffer early death if the ratio is above a cutoff value.

In one embodiment, the disclosure is directed to a method for the determination of mortality associated with kidney disease. The method includes measuring free SDMA in a blood sample from a patient, for example a canine or feline, and determining that the patient has an increased likelihood of death associated with kidney disease when the patient has a blood concentration of SDMA greater than a threshold level. The method may further include the step of measuring creatinine in the blood sample, calculating the ratio [SDMA]/[CRE], wherein the that the patient has an increased likelihood of death associated with kidney disease when the patient has a blood ratio [SDMA]/[CRE] greater than a threshold ratio.

In another aspect, the disclosure is also directed to a device for determining renal function in an animal subject. The device includes a first solid phase having bound thereto an SDMA analog, or an antibody specific for SDMA that has no or substantially no cross-reactivity with one or more compounds selected from asymmetrical dimethylarginine (ADMA), L-arginine, and N-methylarginine; and a second solid phase having bound thereto a creatinine sensing reagent or an antibody specific for creatinine.

In a further aspect, the disclosure is directed to a kit for the determination of renal function in an animal subject. The kit includes one or more creatinine detecting reagents and one or more SDMA detecting reagents, and optionally includes a set of one or more standard values associated with renal function based upon the product of the concentration of creatinine and the concentration of SDMA in one or more blood samples from the animals.

Still further, the disclosure is directed to a computing device having a memory storage comprising software instructions, which when executed, calculates the inverse of the product of the concentration of creatinine and the concentration of free SDMA. The memory storage may also include software instructions for comparing the result of the calculation to one or more standard values representing glomerular filtration rate in an animal subject.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the invention. No attempt is made to show structural details of the invention in more detail than may be necessary for a fundamental understanding of the invention and various ways in which it may be practiced.

DESCRIPTION

Figure 1:
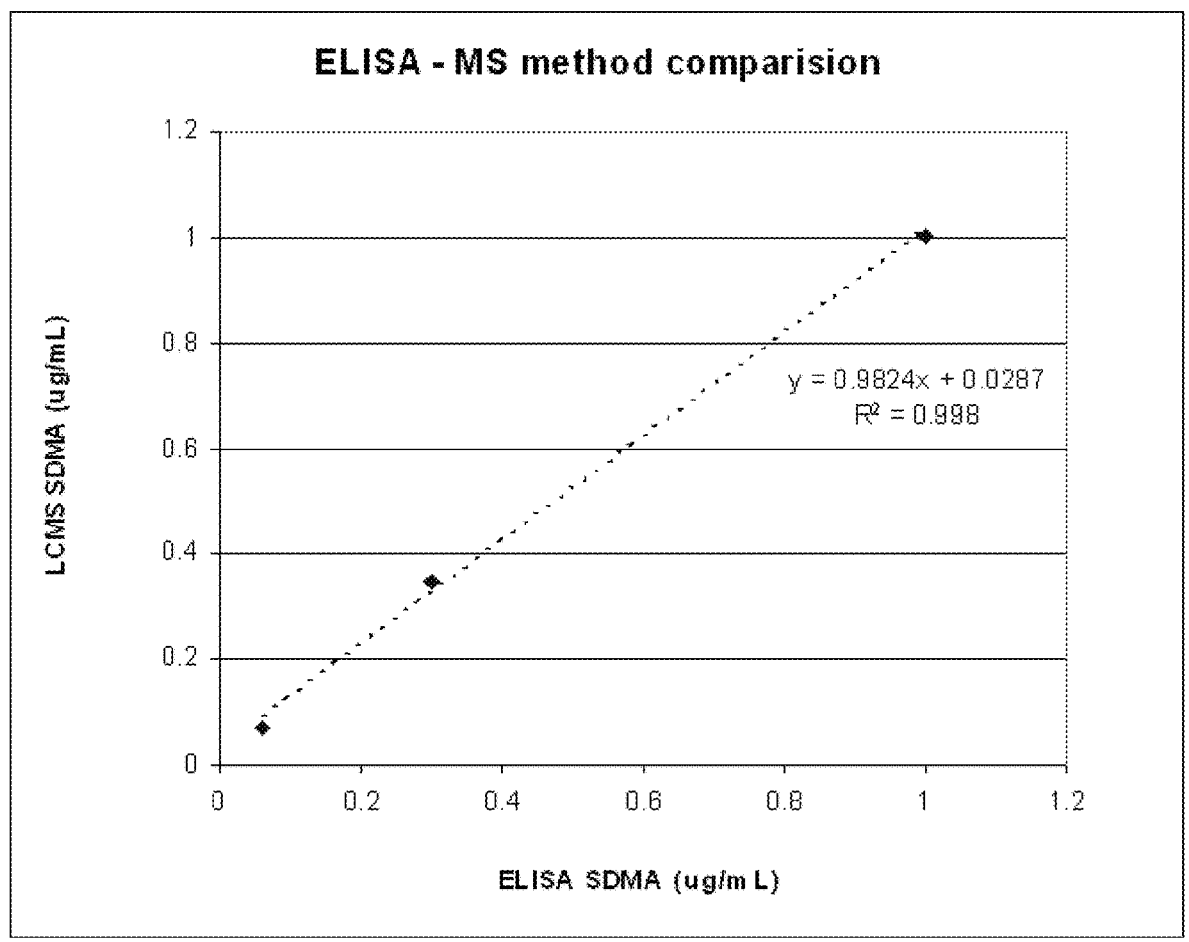
FIG. 1 is a graph comparing the results of an ELISA method of detecting SDMA with mass spectroscopy.

In its various aspects, the disclosure is directed to the determination, diagnosis, progression and prognosis of kidney disease and mortality associated with kidney disease. The disclosure includes a method for determining renal function, in particular estimating glomerular filtration rate (GFR), in an animal. GFR can be useful in the diagnosis and treatment of kidney disease or dysfunction.

In various aspects, the disclosure is directed to the use of free Symmetrical dimethylarginine (SDMA) and creatinine in blood samples from animals, in particular cats and dogs, to determine glomerular filtration rate and kidney disease. In one aspect, the product of the concentrations of creatinine and free SDMA in blood samples from an animal can be correlated to GFR and renal disease. For instance, the inverse of the product of the concentrations of creatinine and free SDMA (e.g., 1/[creatinine][SDMA]) is used and unexpectedly results in a much higher precision for the measurement of glomerular filtration rate than the use of either measurement alone. Therefore, the disclosure includes a method for measuring the concentration of free SDMA in a blood sample from the animal subject; measuring the concentration of creatinine in a blood sample from the animal subject; and determining the glomerular filtration rate of the animal subject by comparing the inverse of the product of the concentration of creatinine and the concentration of free SDMA to one or more standard values for glomerular filtration rate in the animal subject. Other aspects of the disclosure include the use of SDMA concentration alone or in a ratio of SDMA concentration to creatinine concentration for the determination of kidney disease as described herein.

SDMA is the structural isomer of the endogenous nitric oxide synthetase (NOS) inhibitor asymmetric dimethylarginine (ADMA). Both ADMA and SDMA derive from intranuclear methylation of L-arginine residuals and are released into the cytoplasm after proteolysis. SDMA is produced by protein-arginine methyltransferase 5 (PRMT 5) and PRMT 7. Proteins carrying methylarginines, such as SDMA, monomethylarginine and ADMA, play a role in RNA processing, protein shuttling and signal transduction (Bedford and Richard, Mol. Cell, 2005, Apr. 29, 18(3):263-72). Free SDMA resulting from the degradation of such methylated proteins is mainly eliminated by renal excretion, whereas ADMA is largely metabolized. ADMA is strongly correlated with risk factors for coronary artery disease (CAD) such as hypertension, hypercholesterolemia, hyperhomocysteinemia, insulin resistance, age, and mean arterial pressure. SDMA is correlated with parameters of renal function, such as glomerular filtration rate (GFR), inulin clearance, and creatinine clearance.

Accordingly, one aspect the disclosure is directed to a method for estimating the glomerular filtration rate of an animal subject by using the values for both the concentration of free SDMA and the concentration of creatinine in serum. The inverse of the product of the values (e.g., 1/([creatinine][SDMA]) correlates linearly to GFR more precisely than the concentration of creatinine or SDMA alone.

A number of terms are defined below:

Ab is antibody.

ADMA is asymmetrical dimethylarginine. The structure of ADMA is:

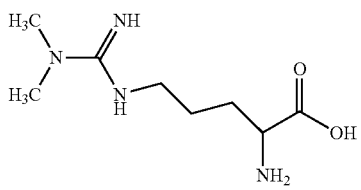

BUN is blood urea nitrogen.
BSA is bovine serum albumin.
CMIA is chemiluminescent magnetic immunoassay.
DCM is dichloromethane.
DIPEA is N,N-diisopropylethylamine.
DMF is dimethyl formamide.
EIA is enzyme immunoassay.
ELISA is enzyme-linked immunosorbent assay.
ESI-MS is electrospray ionization mass spectroscopy.
FPIA is fluorescence polarization immunoassay.
GFR is glomerular filtration rate.
HATU is (1H-7-azabenzotriazol-1-yl)-1,1,3,3-tetramethyl uranium hexafluorophosphate methanamininium.
KLH is keyhole limpet hemocyanin.
MEIA is microparticle enzyme immunoassay.
NOS is nitric oxide synthase.
PBS is phosphate buffered saline.
RIA is radioimmunoassay.
SDMA is symmetrical dimethylarginine. The structure of SDMA is:

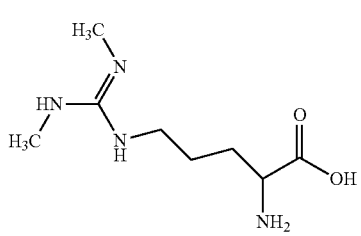

Free SDMA refers to SDMA that is not part of a polypeptide chain. One or more amino acid residues of SDMA can be present in a polypeptide.

SLE is systemic lupus erythematosus.
TFA is trifluoracetic acid.
The structure of arginine is:

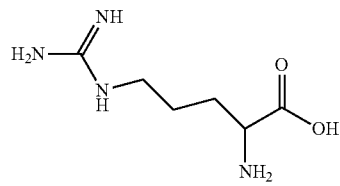 [SMILES: N=C(N)NCCCC(N)C(=O)O]

N-MMA is N-monomethylarginine, or simply N-methylarginine. The structure of N-monomethylarginine is:

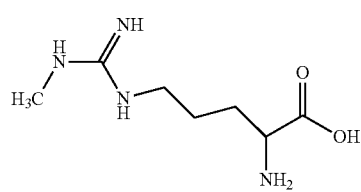

The term "analog," as used herein, generally refers to a compound in which one or more individual atoms have been replaced with a different atom(s) or with a different functional group(s). For example, an analog may be a modified form of the analyte which can compete with the analyte for a receptor, the modification providing a means to join the analyte to another moiety, such as a label or solid support. The analyte analog can bind to an antibody in a manner similar to the analyte.

The term "antibody," as used herein, generally refers to a glycoprotein produced by B lymphocyte cells in response to exposure to an antigen and binds specifically to that antigen. The term "antibody" is used in its broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, an "anti-SDMA," "anti-SDMA antibody portion," or "anti-SDMA antibody fragment" and/or "anti-SDMA antibody variant" and the like include any protein or peptide containing molecule that comprises at least a portion of an immunoglobulin molecule, such as, but not limited to, one complementarity determining region (CDR) of a heavy chain or light chain constant region, a framework region, or any portion thereof.

The term "antibody fragment," as used herein, refers to a portion of a full length antibody, generally the antigen binding or variable domain thereof. Specifically, for example, antibody fragments may include Fab, Fab', F(ab')$_2$, and Fv fragments; diabodies; linear antibodies; single-chain antibody molecules; and multispecific antibodies from antibody fragments.

The term "antigen," as used herein, generally refers to a substance that is capable, under appropriate conditions, of reacting with an antibody specific for the antigen.

The term "analyte," as used herein, generally refers to the substance, or set of substances in a sample that are detected and/or measured.

The term "animal," as used herein, generally refers to any animal, e.g., a human, or a non-human animal such as a cat, a dog, or a horse.

The term "blood sample," as used herein, generally refers to any blood-derived fluid sample, including but not limited to whole blood, plasma, and serum. To provide serum for use in the methods of the disclosure, one or more serum samples are obtained from the animal subject. The serum samples can be, for example, obtained from the animal subject as blood samples, then separated to provide serum. In certain embodiments, the serum can be measured without separation from blood. As the person of skill in the art will appreciate, a single obtained sample can be divided or otherwise used to do both concentration measurements. Alternatively, a plurality of samples can be obtained from the animal subject, with (at least) one sample being measured for creatinine concentration, and (at least) one sample being measured for free SDMA concentration. In certain such cases, the samples are obtained from the animal at about the same time (e.g., within 60 minutes, within 30 minutes, or even within 10 minutes of one another).

The term "cross-reactivity," as used herein, generally refers to the ability of an individual antigen binding site of an antibody to react with more than one antigenic determinant or the ability of a population of antibody molecules to react with more than one antigen. In general, cross reactions arise because (i) the cross reacting antigen shares an epitope in common with the immunizing antigen or (ii) it has an epitope which is structurally similar to one on the immunizing antigen (multispecificity).

The term "immunoassay," as used herein, generally refers to a test that employs antibody and antigen complexes to generate a measurable response. An "antibody:antigen complex" may be used interchangeably with the term "immunocomplex." Immunoassays, in general, include noncompetitive immunoassays, competitive immunoassays, homogeneous immunoassays, and heterogeneous immunoassays. In "competitive immunoassays," unlabeled analyte (or antigen) in the test sample is measured by its ability to compete with labeled antigen in the immunoassay. The unlabeled antigen blocks the ability of the labeled antigen to bind because the binding site on the antibody is already occupied. In "competitive immunoassays," the amount of antigen present in the test sample is inversely related to the amount of signal generated from the label. Conversely, in "noncompetitive immunoassays," also known as "sandwich" immunoassays, the analyte is bound between two highly specific antibody reagents to form a complex and the amount of antigen is directly proportional to the amount of signal associated with the complex. Immunoassays that require separation of bound antibody:antigen complexes are generally referred to as "heterogeneous immunoassays," and immunoassays that do not require separation of antibody:antigen complexes are generally referred to as "homogeneous immunoassays." One of skill in the art would readily understand the various immunoassay formats.

The term "immune complexes," as used herein, generally refers to the complexes formed by the binding of antigen and antibody molecules, with or without complement fixation. When one of either the antibody or antigen is labeled, the label is associated with the immune complex as a result of the binding between the antigen and antibody. Therefore, when the antibody is labeled, the label becomes associated with the antigen as a result of the binding. Similarly, when the antigen is labeled (e.g., an analyte analog having a label), the label becomes associated with the antibody as a result of the binding between the antigen and the antibody.

The term "label," as used herein, refers to a detectable compound, composition, or solid support, which can be conjugated directly or indirectly (e.g., via covalent or non-covalent means, alone or encapsulated) to an antibody, SDMA analog, or antigen of the disclosure. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label employed in the current disclosure could be, but is not limited to: alkaline phosphatase; glucose-6-phosphate dehydrogenase ("G6PDH"); horse radish peroxidase (HRP); chemiluminescers such as isoluminol, fluorescers such as fluorescein and rhodamine compounds; ribozymes; and dyes. The label may also be a specific binding molecule which itself may be detectable (e.g., biotin, avidin, streptavidin, digoxigenin, maltose, oligohistidine, 2, 4-dinitrobenzene, phenylarsenate, ssDNA, dsDNA, and the like). The label may be bound to another molecule or solid support and that is chosen for specific characteristics that allow detection of the labeled molecule. The utilization of a label produces a signal that may be detected by means such as detection of electromagnetic radiation or direct visualization, and that can optionally be measured.

The term "monoclonal antibody," as used herein generally refers to an antibody obtained from a population of substantially homogeneous antibodies, i.e., the individual antibodies comprising the population are identical. Monoclonal antibodies are highly specific, being directed against a single antigenic site. In contrast to polyclonal antibody preparations, which typically include different antibodies directed against different epitopes, each monoclonal antibody is directed against a single epitope on the antigen. The modifier "monoclonal" merely refers to the character of the antibody and is not to be construed as requiring production of the antibody by any particular method. Specifically, for example, monoclonal antibodies may be made by hybridoma methodologies, or may be made by recombinant DNA methods, or may be isolated from phage antibody libraries using known techniques.

The term "polypeptide," as used herein, generally refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the disclosure, treated as a subclass of the polypeptides and polypeptide derivatives.

The term "solid support," as used herein, refers to a non-aqueous matrix to which the antibody or SDMA analog of the present disclosure can adhere. Example of solid support include supports formed partially or entirely of glass (e.g., controlled pore glass), synthetic and natural polymers, polysaccharides (e.g., agarose), polyacrylamides, polystyrene, polyvinyl alcohols and silicones, magnetic particles, latex particles, chromatographic strips, microtiter polystyrene plates, or any other substances that will allow bound antigens and/or antibodies to be washed or separated from unbound materials. In certain embodiments, depending on the application, the solid support can be the well of an assay plate or can be a purification column (e.g., an affinity chromatography column).

"Receptor" refers to any compound or composition capable of recognizing a particular spatial and polar organization of a molecule, e.g., epitopic or determinant site. Illustrative receptors include antibodies, Fab fragments, and the like.

"Binding specificity" or "specific binding" refers to the substantial recognition of a first molecule for a second molecule, for example a polypeptide and a polyclonal or monoclonal antibody, or an antibody fragment (e.g. a Fv, single chain Fv, Fab', or F(ab')2 fragment) specific for the polypeptide. For example, "specificity," as used herein, generally refers to the ability of an individual antibody combining site to react with only one antigenic determinant or the ability of a population of antibody molecules to react with only one antigen. In general, there is a high degree of specificity in antigen-antibody reactions. Antibodies can distinguish differences in (i) the primary structure of an antigen, (ii) isomeric forms of an antigen, and (iii) secondary and tertiary structure of an antigen. Antibody-antigen reactions that exhibit high specificity exhibit low cross reactivity.

"Substantial binding" or "substantially bind" refers to an amount of specific binding or recognizing between molecules in an assay mixture under particular assay conditions. In its broadest aspect, substantial binding relates to the difference between a first molecule's incapability of binding or recognizing a second molecule, and the first molecules capability of binding or recognizing a third molecule, such that the difference is sufficient to allow a meaningful assay to be conducted distinguishing specific binding under a particular set of assay conditions, which includes the relative concentrations of the molecules, and the time and temperature of an incubation. In another aspect, one molecule is substantially incapable of binding or recognizing another molecule in a cross-reactivity sense where the first molecule exhibits a reactivity for a second molecule that is less than 25%, less than 10%, less than 5% or less than 1% of the reactivity exhibited toward a third molecule under a particular set of assay conditions. Specific binding can be tested using a number of widely known methods, e.g., an immunohistochemical assay, an enzyme-linked immunosorbent assay (ELISA), a radioimmunoassay (RIA), or a western blot assay.

The term "salt," as used herein, means a salt formed between an acid and a basic functional group of a compound. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "salt" also refers to a salt formed between a compound having an acidic functional group, such as a carboxylic acid functional group, and an inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

In certain methods described herein, the glomerular filtration rate of the animal subject is determined by comparing the results of an equation that considers the product of the concentration of creatinine and the concentration of free SDMA in blood samples from an animal subject. For example, to determine GFR, the inverse of the product of the concentration of creatinine and the concentration of free SDMA can be compared to one or more standard values that correlate to glomerular filtration rate in the animal subject. As described in more detail in Example 6, below, there is a linear relationship between GFR and the inverse of the product of creatinine concentration and free SDMA concentration. Accordingly, the person of skill in the art can establish a linear equation between GFR and 1/([creatinine][SDMA]) for the animal subject (e.g., using other animals of the same species or type), and use that equation to provide the standard values for comparison with the inverse of the product of the measured concentrations. As the person of skill in the art will appreciate, comparison with standard values can include merely using the equation to calculate GFR from the value of 1/([creatinine][SDMA]). Alternatively, a set of standard values of the inverse of the product of concentrations of creatinine and free SDMA for a set of known GFR values can be determined; and the GFR of the animal subject can be determined by comparing the inverse of the product of its measured concentrations of creatinine concentration and free SDMA to the standard values. In certain embodiments, the determining step is performed using a microprocessor programmed to compare the inverse of the product of the concentrations of creatinine and free SDMA to the equation or to the one or more standard values. The microprocessor is usually a component of a computing device containing memory storage containing software instructions, which when executed, carry out the function of calculating the equation and performing the comparison based upon input from an operator or a detection device.

As the person of skill in the art will appreciate, comparison of the inverse of the product of the concentration of creatinine and the concentration of free SDMA to one or more standard values for the inverse of the product that correlate to glomerular filtration rate also includes numerical comparisons that are mathematically equivalent to such comparison. For example, comparisons using values that are representative of {constant×(1/([creatinine][SDMA])} and/or [constant×GFR] are also contemplated. For example, the comparison can be accomplished based upon the product alone ([creatinine][SDMA]). In addition, one skilled in the art will appreciate that inserting a factor in the denominator and/or numerator of the quotient (1/([creatinine][SDMA]) will not change the strength of its relationship with GFR (e.g., 2/([SDMA][creatinine]), 1/(2[SDMA][creatinine]) or 5/(3[SDMA][creatinine]). Similarly, the relationship of ([creatinine][SDMA]) with 1/GFR is likewise contemplated.

In another aspect, the disclosure is directed to estimating GFR using the formula:

$$GFR \cong 1/(CRE \times SDMA).$$

Based upon experimental results, this formula has a correlation coefficient (R-square) of about 0.8347. When the equation is generalized as follows:

$$GFR \cong (CRE)^P \times (SDMA)^Q$$

the exponents (P and Q) that maximize the correlation coefficient are $P \cong -1.551102$ and $Q \cong 0.2204409$. The R-square for this set of exponents is 0.9116. As understood by one of skill in the art, P and Q are weighting factors that can be adjusted to maximize the correlation coefficient.

Slightly changing the exponents does not seem to affect the R-square in a significant way. For example, when for P=−1.5 and Q=−0.25, the R-square is 0.9114. For simplicity, an ideal power transformation for creatinine and SDMA levels in relation to GFR level takes the form:

$$GFR \approx (CRE)^{-1.5} \times (SDMA)^{-0.25}$$

In various embodiments, the weighting factors P and Q can be adjusted further. For example, P can vary from about −5 to less than almost 0 (e.g., −0.01). In other words, P can vary from about −5 to any value between −5 and 0, but not including zero. In specific non-limiting examples, P can vary from about −4.0 to −0.1, about −3.0 to −0.5, about −2.0 to −1.0., and about −1.0 to 0, but not including 0). Independently, Q can vary from −2.5 to almost 0 (e.g., −0.01). In other words, Q can vary from about −2.5 to any value between −2.5 and 0, but not including zero. In specific non-limiting examples, Q can vary from about −2.0 to 0.1, about −1.5 to −0.15, about −1.0 to −0.2, about −1.5 to −0.5, about −1.2 to −0.8,and about −1.0 to 0, but not including 0.

In certain embodiments, the glomerular filtration rate is used to determine renal function of the animal subject. For example, the glomerular filtration rate can be used to diagnose kidney disease or dysfunction in the animal subject. Renal diseases and disorders (e.g., kidney impairment, renal insufficiency, chronic kidney disease, glomerulonephritis, diabetic nephropathy, interstitial nephritis, polycystic kidney disease, and hypertensive kidney disease) tend to decrease overall renal function, including GFR, and can be diagnosed using the methods described herein. For example, glomerular filtration rate in an animal known to have or suspected of having disease can be compared to the glomerular filtration rate in one or more, e.g., a population of healthy subjects. Renal diseases and disorders can be predicted when the subject rate is less than the rate of the healthy subject(s). In certain embodiments, if the glomerular filtration rate is statistically significantly less than the average value for a population of healthy animals of the same species (i.e., as estimated using the correlation with [creatinine]$^P$ [SDMA]$^Q$), kidney disease or dysfunction can be diagnosed. In a non-limiting example, the GFR of the subject animal is statistically significantly less than the average GFR of the healthy population when the difference is greater than two standard deviations.

Figure 7:
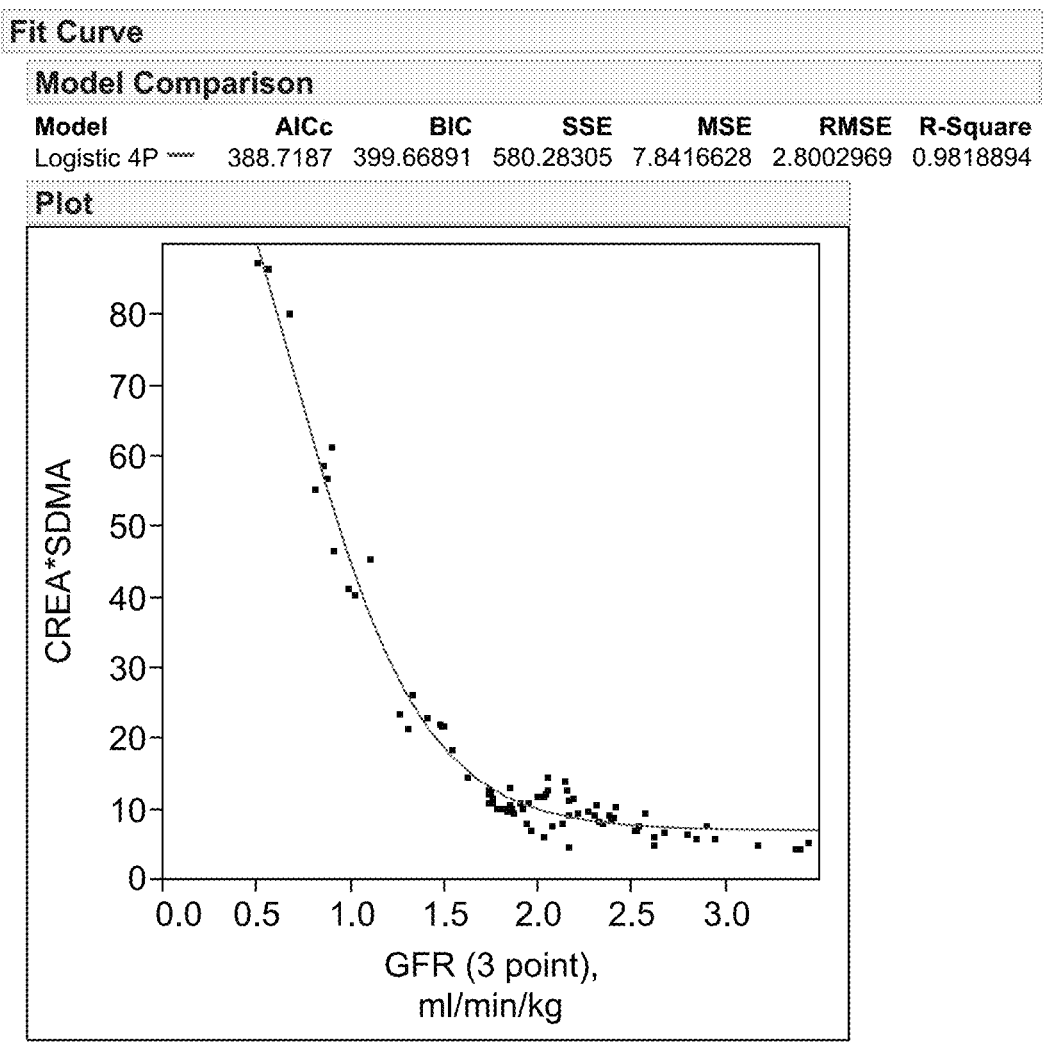
FIG. 7 is a plot of [Creatinine]*[SDMA] vs. GFR for a set of canine serum samples, as described in Example 6.

In one aspect the disclosure is directed to a collection of standard values for the equation that correlate to GFR or kidney disease or dysfunction. The collection may be associated with a standard curve that correlates the value of the equation with GFR as shown in FIG. 7. In other embodiments, the values or standard curve are associated with kidney disease or dysfunction. The standard values can be represented in the form of a table or chart that is referenced by a health care provider or in the machine readable instructions associated with a computing device as described herein.

In another aspect, kidney disease or disorder can be diagnosed from an equation including the product of the concentrations of creatinine and SDMA as describe above without the intermediate step of determining GFR. Accordingly, using the equation to generate a value, the value can be compared to a standard value or a set of standard values known to be associated with disease or dysfunction. In one aspect, the calculating is conducted at reference laboratory and the value from the equation can be reported to a physician, veterinarian, or other animal health care provider. The provider can compare the value to one or more known set of values that correlate to kidney disease or dysfunction. In another aspect, the reference laboratory can conduct the comparison, for example on a computing device, and report the ultimate result to the physician.

In another aspect, the disclosure is directed to the diagnosis of a kidney disease or disorder, such as Chronic Kidney Disease (CKD) by combining the values associated with SDMA and creatinine concentration in samples taken from animals, for example serum samples. The formula uses cut-off values for SDMA and creatinine derived from threshold sample concentrations that are indicative of renal disease. The cut-off or threshold concentrations can be determined by sampling a population of animals and relating the concentrations of SDMA and creatinine in the populations to a disease state as is known in the art. In various embodiments, the SDMA cut off ($SDMA_{CUT}$) may be between about 10 and about 20 μg/dL, more particularly about 10, 11, 12, 13, 14, 15, 16, 17, 18, 19 or 20 μg/dL, and even more particularly, about 14 μg/dL. The creatinine cut-off may be between about 1.3 and about 2.5 or between about 1.7 and about 2.8 mg/dL, more particularly about 1.7, 1.8, 1.9, 2.0, 2.1, 2.2, 2.3, 2.4, 2.5, 2.6, 2.7, and 2.8 mg/dL. Once the cut-off values are determined, a value (C) representing a combination of the concentrations of SDMA and creatinine in a patient sample compared to the cut-off values for SDMA and creatinine can be obtained with the following formula: $C = [SDMA]/SDMA_{CUT} + [CRE]/CRE_{CUT}$. If C is greater than $C_{CUT}$, a patient is diagnosed with kidney disease.

Figure 13:
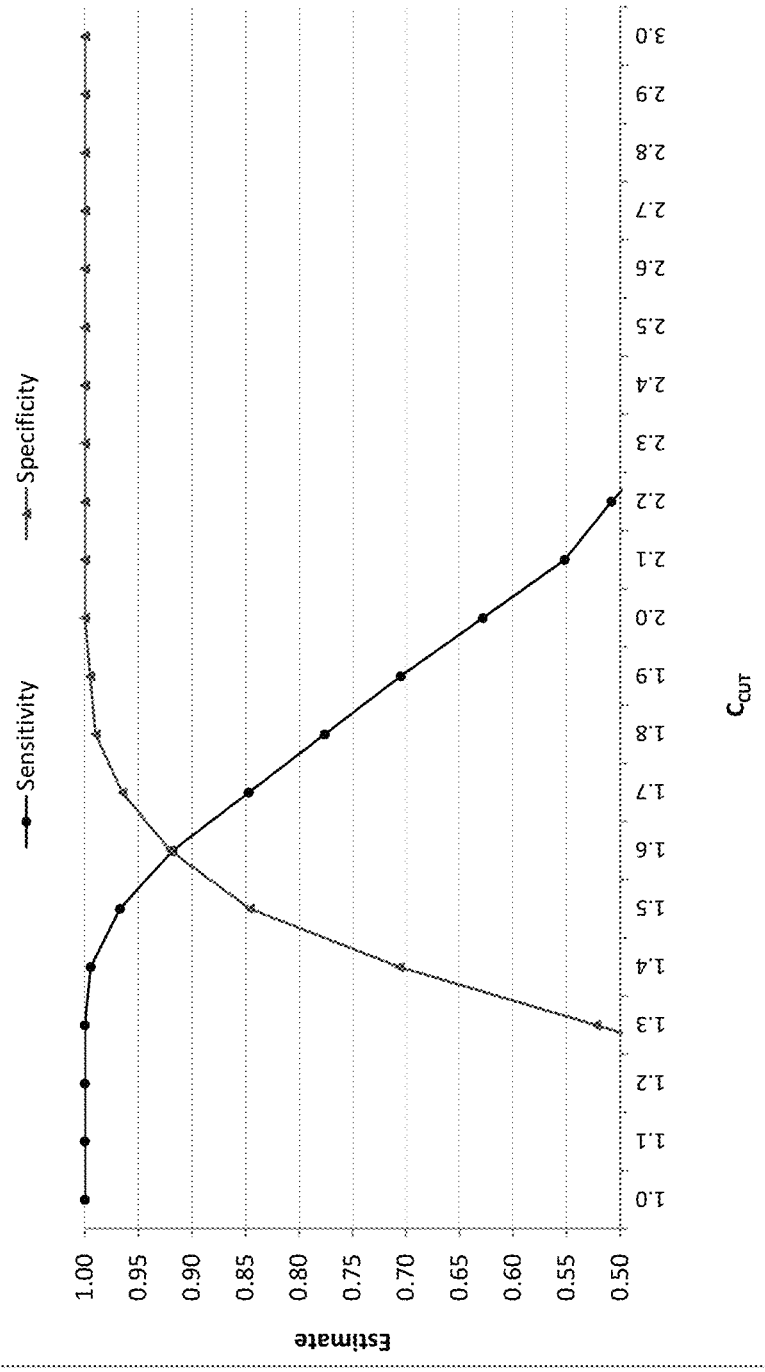
FIG. 13 is a graph showing the improved specificity and sensitivity in a method for determining kidney disease.

$C_{CUT}$ is determined by choosing a value having an optimal combined sensitivity and specificity for the assay. FIG. 13 illustrates how different values of $C_{CUT}$ affect specificity and/or sensitivity. $C_{CUT}$ can be chosen to accommodate a desired level of specificity and/or sensitivity for the detection of renal disease. For example, for the data set shown in FIG. 13, both the sensitivity and the specificity of detection exceed 90% when $C_{CUT}=1.6$. Typically, higher values of $C_{CUT}$ result in higher specificity but lower sensitivity. Conversely, lower values of $C_{CUT}$ will typically result in lower specificity but higher sensitivity.

The disclosure is also directed to a computing device for performing the calculation described above, for determining GFR, or for diagnosing kidney disease or dysfunction. The computing device includes memory storage for software instructions, which when executed, calculate a value from an equation including the product of the concentration of creatinine and the concentration free SDMA.

In another embodiment, the disclosure is directed to a prognostic method for predicting premature or early death in a patient or animal subject. In accordance with the method, cats have an increased risk of early death when there is an unusual discordance between [SDMA] and [CRE], such that the SDMA value is elevated to a much greater extent than the CRE value, relative to their respective normal cutoff values. In one embodiment, the method provides for the prognosis of early death when the ratio [SDMA]/[CRE] in serum is greater than a certain threshold value T.

For example, when [SDMA] is expressed in μg/dL (micrograms/deciliter) and [CRE] is expressed in mg/dL (milligrams/deciliter), T may assume a value of about 4 to about 10 (i.e., about 4 μg/dL SDMA:1 mg/dL creatinine to about 10 μg/dL SDMA:1 mg/dL creatinine). In various embodiments, the threshold value T may be between about 7 and 20, more particularly about 7, 8, 9, 10, 11, 12, 13, 14, 15, 16, 17, 18, 19 or 20. One of skill in the art will understand that if the concentration of CRE and/or SDMA are expressed in different units of measurement than the units given above, the threshold value of [SDMA]/[CRE] may change accordingly and proportionally, without affecting the spirit and prognostic utility of the method.

Furthermore, the risk of premature death may increase with increasing values of the ratio [SDMA]/[CRE]. For example, an individual having [SDMA]/[CRE]=40 may have a higher risk of premature death than an individual with [SDMA]/[CRE]=12.

In addition, an unusually sudden increase in [SDMA] is prognostic for an increased risk of early death. Similarly, unusually high values of [SDMA] are prognostic for an increased risk of early death. For example, unusually high values of [SDMA] in cats may be values above about 25 μg/dL, above about 30 μg/dL, or above about 30 μg/dL.

Figure 19:
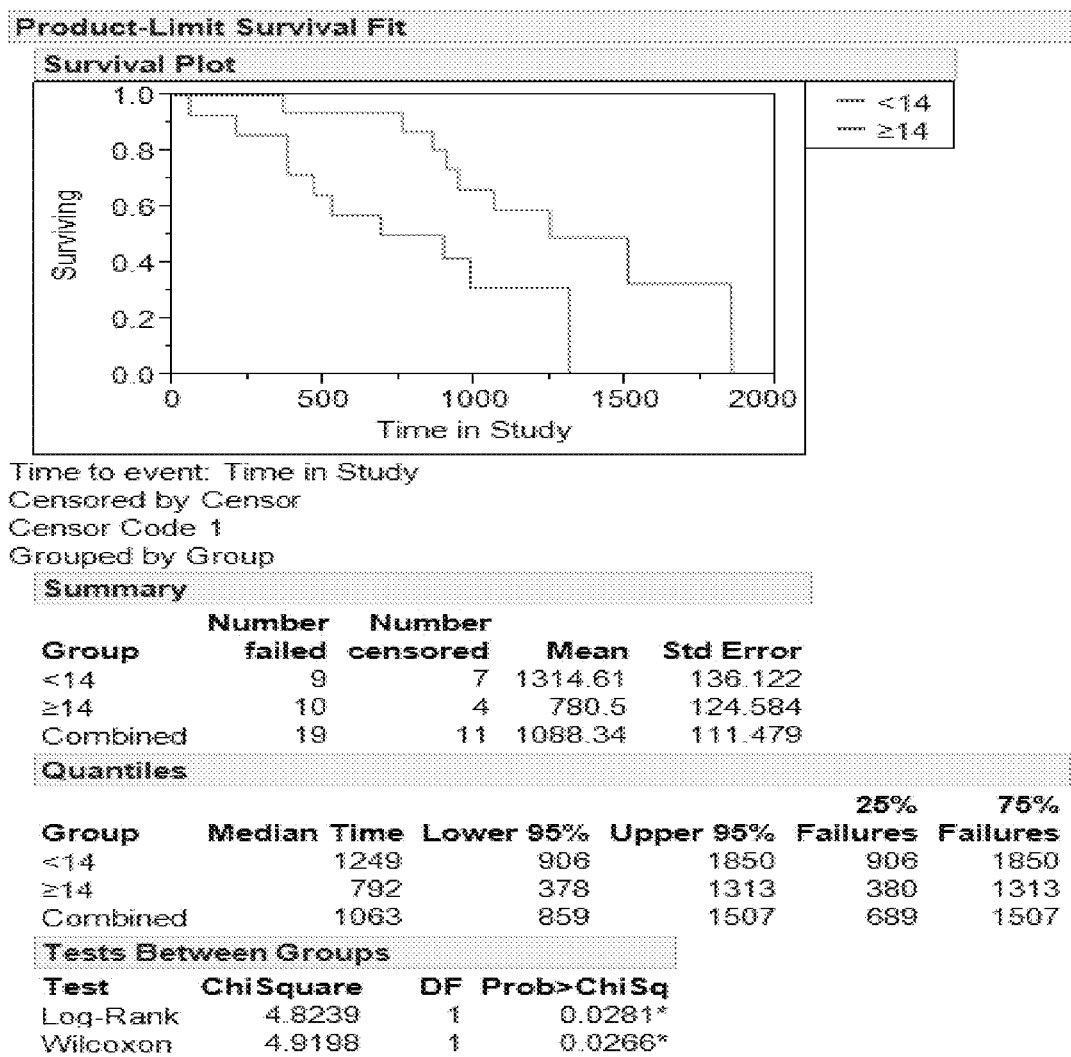
FIG. 19 is a Kaplan-Meier survival curve that shows that cats having a serum SDMA concentration of less than 14 μg/dL survive approximately 1.6 times longer than cats with concentrations of greater than 14 μg/dL.
Figure 20:
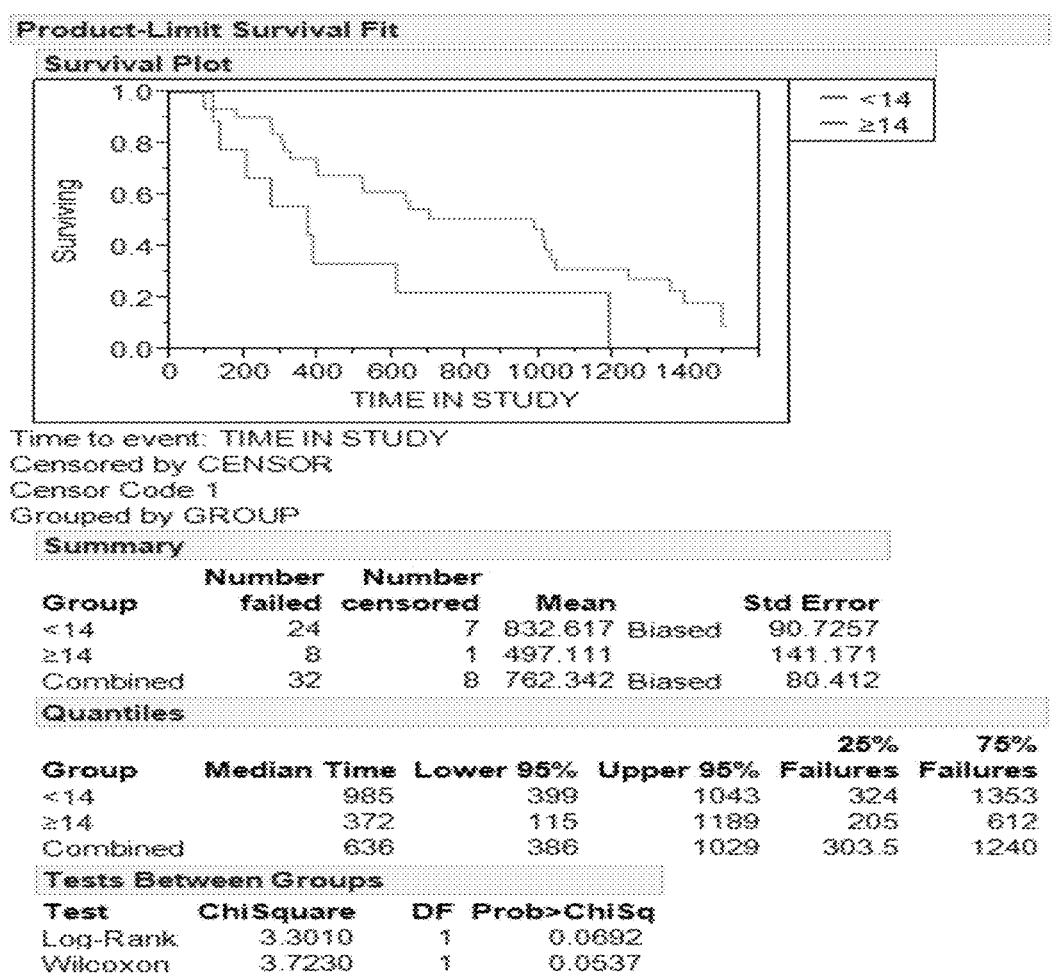
FIG. 20 is a Kaplan-Meier survival curve that shows that dogs having a serum SDMA concentration of less than 14 μg/dL survive approximately 2.6 times longer than dogs with concentrations of greater than 14 μg/dL.

In one aspect, the disclosure is directed to serum SDMA concentration that is predictive of mortality. For example, as shown in FIGS. 19 and 20, SDMA serum concentration greater than 14 μg/dL have been shown to have been associated with mortality in cats and dogs. Accordingly, the disclosure is directed to identifying an appropriate SDMA concentration cut off value that is the most predictive of mortality. In one aspect, the cut off is in the range from about 10-20 μg/dL, more particularly about 12-18 μg/dL, or about 14-16 μg/dL. Identification of an appropriate cut-off concentration can be determined, for example, by measuring the concentration of serum SDMA in each member of a group of dogs or cats, and repeating the measurement over a period of several month or years until the death of each member of the group. Optionally, all dogs or cats in the group have been diagnosed with CKD. Different candidate SDMA concentration cut off values threshold values are tested for their ability to predict a decreased survival time. Such testing can be performed. For example, through the use of Kaplan-Meier Survival Curves.

Figure 14:
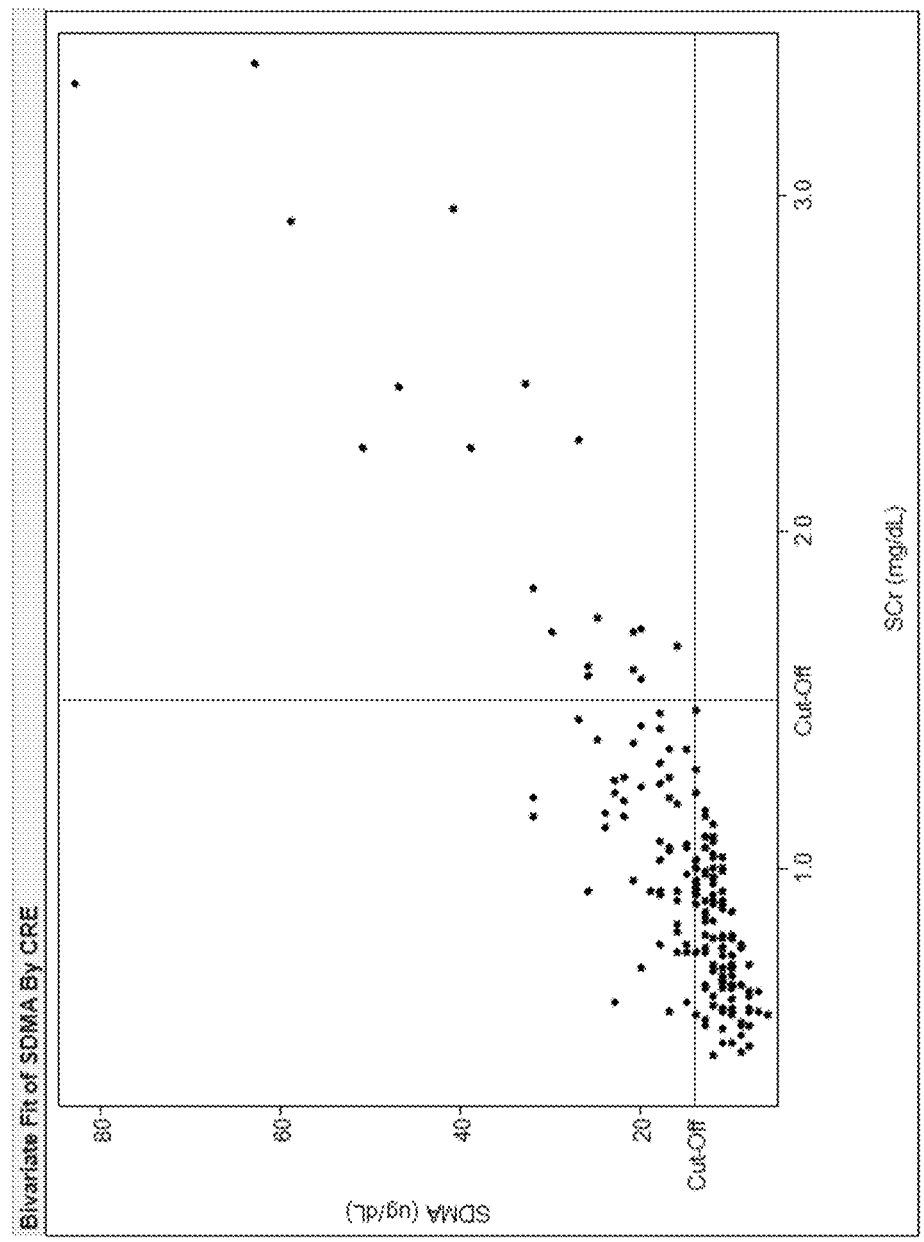
FIG. 14 shows the correlation between SDMA (μg/dL) and creatinine (mg/dL) in dogs.

Kaplan-Meier Survival Curves can be used to represent the prediction of mortality. The Kaplan-Meier curves are a general way of dealing with differing survival times (times-to-event), especially when not all the subjects continue in the study. Each subject is characterized by three variables: their serial time, their status at the end of their serial time (event occurrence or censored); the study group they are in (e.g., SDMA < or ≥14). The event is usually a clinical outcome such as death, disappearance of a tumor, etc. The time of the study is the period of time that the event of interest is likely to occur from the starting point. The end of the study is reached before all participants have presented this event, even if the outcome of the remaining participants is unknown. FIGS. 19 and 20 are Kaplan-Meier survival curves that show that cats and dogs having serum SDMA concentrations of less than 14 μg/dL survive approximately 1.6 and 2.6 times longer (respectively) than cats and dogs with concentrations of greater than or equal to 14 μg/dL. In another aspect, the disclosure is directed to a method of determination of ratio of creatinine to SDMA in healthy and diseased animals, and the use of the ratio for the determination of kidney disease and mortality associated with kidney disease. For instance, in healthy animals, the concentration of SDMA (μg/dL) and creatinine (mg/dL) is generally in a ratio ranging from about 4:1 to 10:1 (ug/dL: mg/dL). However, in some chronic kidney disease patients, SDMA values are significantly higher than corresponding creatinine values, which can indicate the progression of disease. Accordingly, discordance in the SDMA:creatinine ratio may be predictive of mortality in animals. As shown in FIG. 14, there is strong correlation between SDMA and creatinine, and the normal ratio is less than 10 (μg/dL:mg/dL). However, a ratio of SDMA concentration (μg/mL) to creatinine (mg/dL) of greater than 10 indicates advanced kidney disease, leading often to death.

Figure 15:
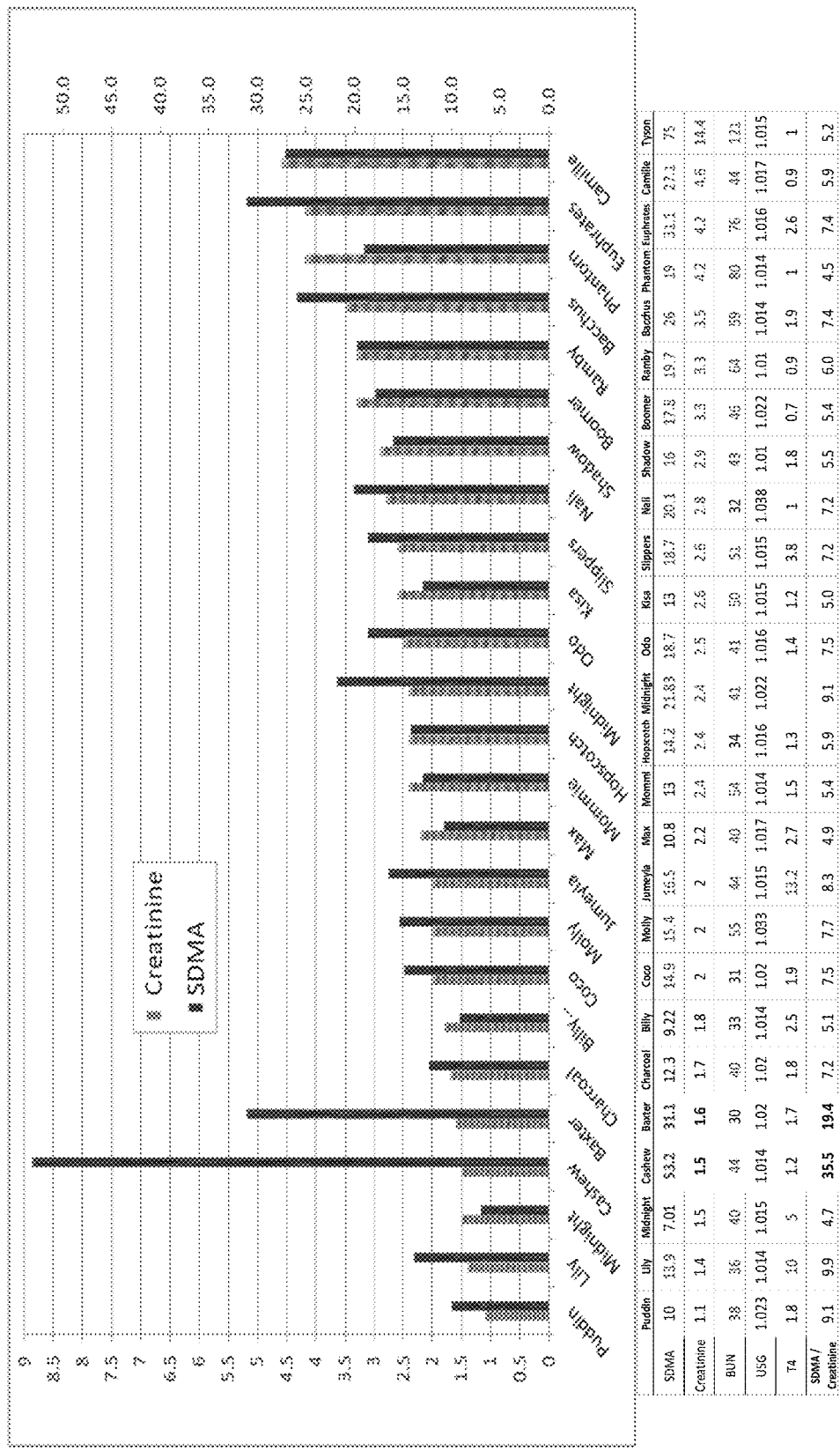
FIG. 15 shows the serum concentration of creatinine and SDMA in a population of cats.
Figure 16:
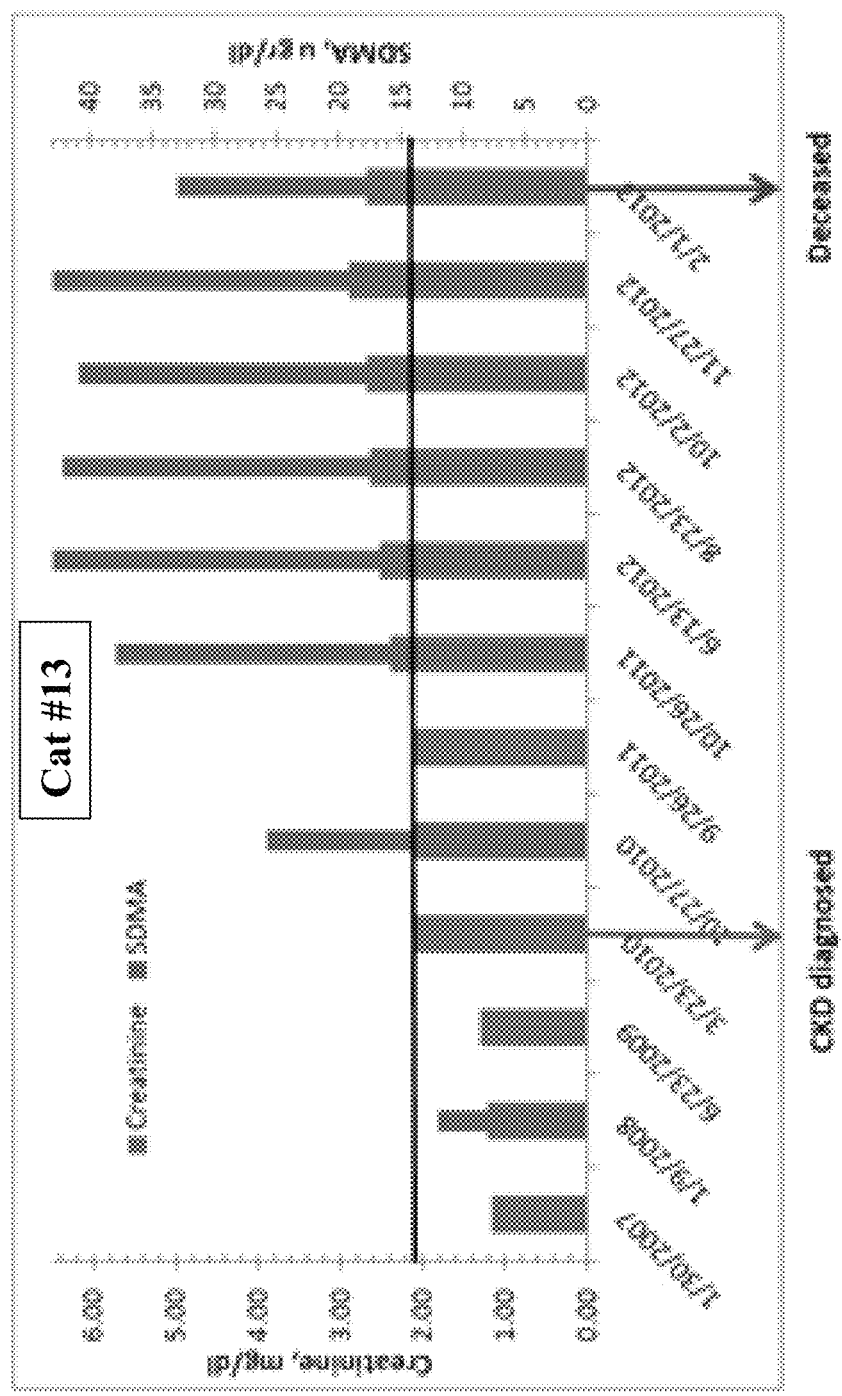
FIG. 16 shows the serum concentration of creatinine and SDMA in a cat over a period of several years.
Figure 17:
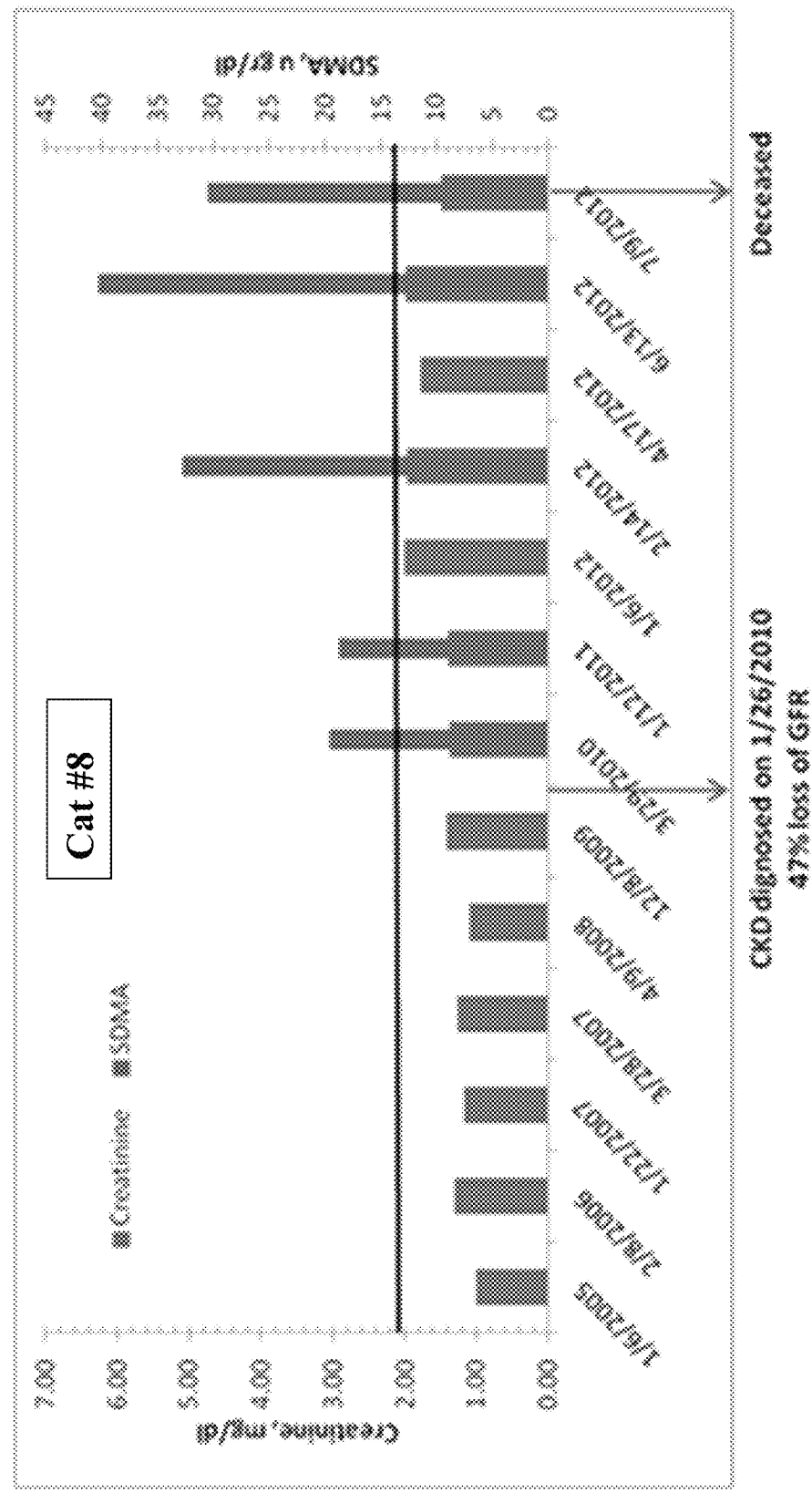
FIG. 17 shows the serum concentration of creatinine and SDMA in a cat over a period of several years.
Figure 18:
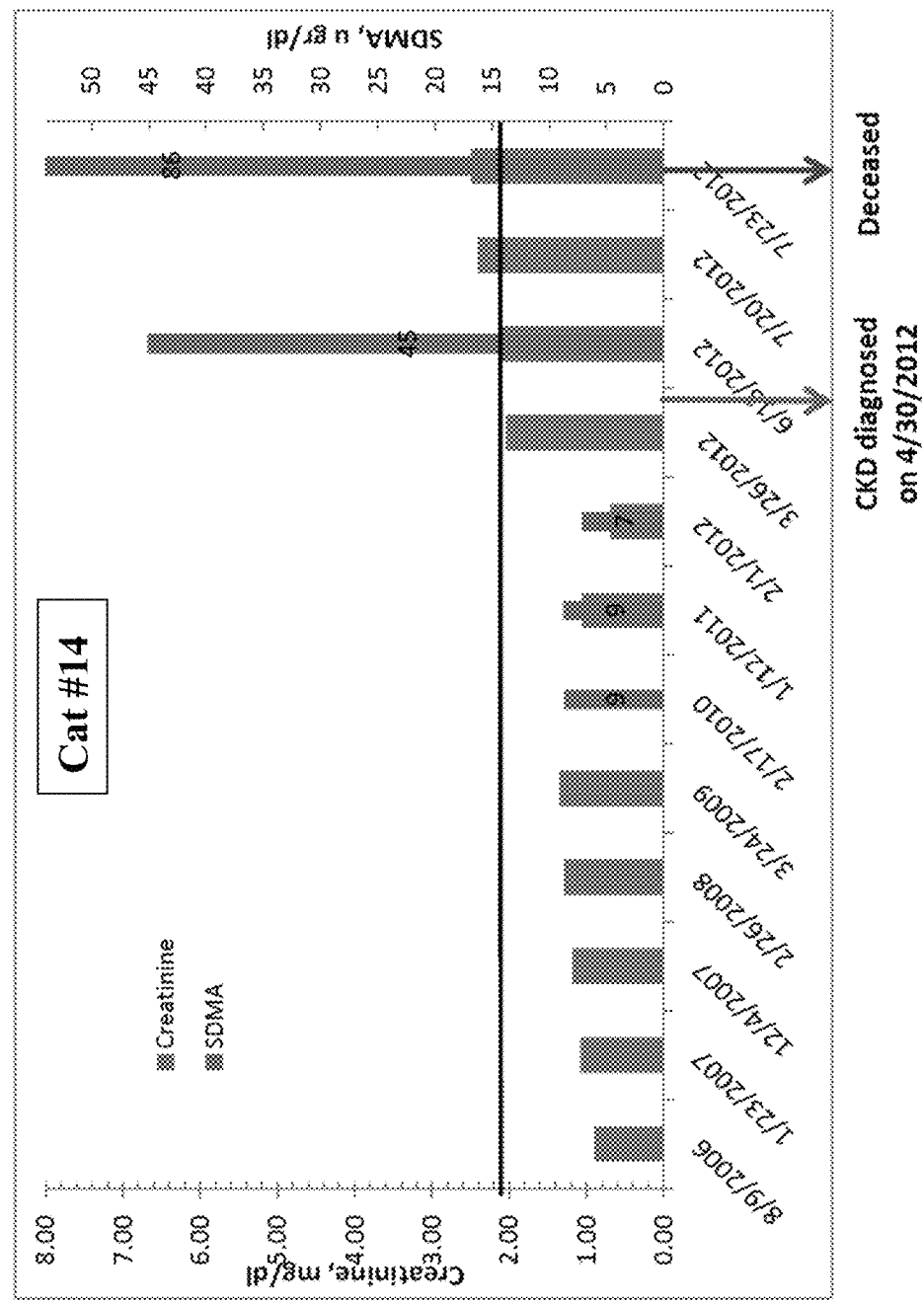
FIG. 18 shows serum concentration of creatinine and SDMA in a cat over a period of several years.

Accordingly, use of the ratio of SDMA concentration to creatinine concentration in serum is predictive of disease and/or mortality. Therefore, the disclosure includes a determining or prognosing kidney disease or death associated with kidney disease. The method includes determining the concentration of SDMA and creatinine in blood, e.g., serum, sample from animals, in particular cats and dogs. Once the concentrations are determined a ratio of SDMA and creatinine can be compared to a cut-off ratio to determine the presence, extent or progression of kidney disease and the likelihood of death as a result of kidney disease. The cut-off ratio may be about 5-15 (μg/dL SDMA:mg/dL creatinine), more particularly about 7-13 or about 9-11, and even more particularly about 10. Animals having an SDMA:creatinine ratio of greater than 10 can be characterized as having an increased likelihood of premature death. Generally, the higher the ratio, the higher the likelihood of imminent death. For example, FIG. 15 shows SDMA: creatinine ratio for a population of cats. Two cats had ratios of about 19 and 34, and each died within the period of the study. FIGS. 16, 17 and 18 show the result of a longitudinal study of three cats that died within about two years after their ratios were identified as greater than about 10. One of these cats died within about one month of ratio being identified as greater than 20 (FIG. 18).

Once kidney disease or dysfunction is diagnosed, the method can include treating the animal subject for kidney disease or dysfunction. Treatments can include, for example, dialysis, kidney transplant, antibiotic therapy (e.g., if kidney dysfunction is due to an underlying infection), prescription diets; treatment of an underlying systemic inflammatory, infectious, or neoplastic disease (e.g., if kidney dysfunction is due to protein losing nephropathy); administration of fomepazole or ethanol (e.g., in cases of ethylene glycol toxicity); administration of ACE inhibitors, moderately protein-restricted diet and/or omega-3 fatty acid supplementation (e.g., in case of proteinuria); administration of phosphate binders and/or a phosphorus-restricted diet (e.g., in cases of hyperphosphatemia); treatment with IV fluids, subcutaneous fluid therapy, low protein diet and/or $H_2$ receptor antagonists (e.g., in cases of azotemia); amlodipine, atenolol and/or ACE inhibitors (e.g., in cases of systemic hypertension); bicarbonate and/or citrate (e.g., for acidosis); administration of vitamin D analogues such as calcitriol or 1,25-dihydroxyvitamin D), phosphate binders (preferably not Ca-based) and/or a phosphorus-restricted diet (e.g., in cases of renal secondary hyperparathyroidism); and/or administration of $H_2$ receptor antagonists and/or human recombinant erythropoietin (possibly with iron supplementation) (e.g., in cases of anemia).

In certain embodiments, the concentration of free SDMA is determined using the immunological methods, devices and kits described in U.S. Provisional Patent Application Ser. No. 61/086,870 filed Aug. 7, 2008, U.S. patent application Ser. No. 12/512,479, filed Jul. 30, 2009, and U.S. Patent Application Publication no. 2010/0035274, published Feb. 11, 2010, each of which is incorporated by reference herein in its entirety. The method may include controls, calibrators or standards comprising one or more SDMA analogs. In particular, the method may be accomplished using immunoassay techniques well known to those of skill in the art, including, but not limited to, using microplates and lateral flow devices. Animal subjects from which samples are obtained for detecting SDMA, include human and non-human animals (e.g., companion animals, livestock, etc.) subjects. The determination of disease states associated with the presence or amount of SDMA can be conducted for both human and non-human subjects.

The solid phase assay format is a commonly used binding assay technique. There are a number of assay devices and procedures wherein the presence of an analyte is indicated by the analyte's binding to a conjugate and/or an immobilized complementary binding member. In one particular aspect, the immobilized binding member (e.g., anti-SDMA antibody) is bound, or becomes bound during the assay, to a solid phase such as a reaction well, dipstick, test strip, flow-through pad, paper, fiber matrix or other suitable solid phase material. The binding reaction between free SDMA in the sample and immobilized antibody is determined by adding to the sample an amount of an analog of SDMA, which includes SDMA conjugated to a label. After contacting the mixture of the sample and the SDMA analog to the solid phase, the mixture and solid phase are incubated to allow for binding between the immobilized antibody, the SDMA and the SDMA analog. Following the incubation, unbound reactants are removed from the solid phase. The amount of the label that becomes associated with the antibody through binding of the antibody to the analog is measured. The amount of the label associated with the antibody is inversely proportional to the amount of free SDMA in the sample.

Immobilization of one or more antibodies to SDMA onto a device or solid support is performed so that the antibodies will not be washed away by the sample, diluent and/or wash procedures. One or more antibodies can be attached to a surface by physical adsorption (i.e., without the use of chemical linkers) or by chemical binding (i.e., with the use of chemical linkers). Chemical binding can generate stronger attachment of antibodies on a surface and provide defined orientation and conformation of the surface-bound molecules.

In another embodiment, SDMA antibodies raised in a particular species are bound to a solid support by interaction with an anti-species antibody that is bound to the support. In one particular aspect, anti-SDMA antibodies are raised in rabbits, and the support has bound thereto anti-rabbit antibody that recognizes the anti-SDMA antibody raised in rabbits. In this aspect, the antibody may be in the form of anti-serum obtained from the species. The anti-SDMA antibodies can either be applied to the solid phase having the anti-species antibody prior to adding the sample to the solid phase, or the anti-SDMA antibodies can be mixed with the sample prior to adding the sample to the solid phase. In either case, the anti-SDMA antibodies become bound to the solid phase through binding to the anti-species antibody on the solid phase.

In another embodiment, one or more labeled antibodies can be mixed with a test sample prior to application of the mixture to a solid support. In this case, an SDMA analog can be attached to the solid support so that the analog will not be washed away by the sample, diluent and/or wash procedures. Labeled antibodies in the sample bind to SDMA in the sample and are, therefore, not available for binding with the SDMA analog on the solid support. After application of the mixture to the solid support, and an appropriate incubation, the mixture is washed from the solid support. Antibodies that have not bound to sample SDMA will become bound to the SDMA analog on the solid support. The presence or amount of SDMA in the sample is inversely proportional to the amount of antibody that has become bound to the SDMA analog. The signal associated with the label on the antibody can be measured by the appropriate method.

FIG. 1 shows a comparison of and ELISA method of detecting SDMA in pooled canine sera spiked with SDMA and the detection of SDMA using mass spectroscopy. As shown, the SDMA concentrations values obtained using the ELISA described herein strongly correlate with those obtained using MS.

Detection of the antibody:antigen complexes may be achieved through a variety of techniques well known in the art, such as, for example, turbidimetry, enzymatic labeling, radiolabeling, luminescence, or fluorescence. Immunoassay methodologies are known by those of ordinary skill in the art and are appreciated to include, but not limited to, radioimmunoassay (RIA), enzyme immunoassays (EIA), fluorescence polarization immunoassays (FPIA), microparticle enzyme immunoassays (MEIA), enzyme multiplied immunoassay technology (EMIT) assays, immuno turbidometric or agglutination assays, colloidal gold based immunoassays including lateral flow devices and chemiluminescent magnetic immunoassays (CMIA). In RIA, an antibody or antigen is labeled with radioactivity and used in a competitive or noncompetitive format. In EIA, an antibody or antigen is labeled with an enzyme that converts a substrate to a product with a resulting signal that is measured, such as a change in color. In FPIA, an antigen is labeled with fluorescent label and competes with unlabeled antigen from the specimen. The amount of analyte measured is inversely proportional to the amount of signal measured. In MEIA, a solid phase microparticle is coated with antibodies against an antigen of interest and is used to capture the analyte. The antibody for detection is labeled with an enzyme as in the EIA method. The concentration of analyte measured is proportional to the amount of signal measured. In CMIA, a chemiluminescent label is conjugated to the antibody or antigen, and produces light when combined with its substrate. CMIA can be configured in a competitive or noncompetitive format, and yields results that are inversely or directly proportional to the amount of analyte present, respectively.

The use of reagent-impregnated test strips in specific binding assays is also well-known. In such procedures, a test sample is applied to one portion of the test strip and is allowed to migrate or wick through the strip material. Thus, the analyte to be detected or measured passes through or along the material, possibly with the aid of an eluting solvent which can be the test sample itself or a separately added solution. The analyte migrates into a capture or detection zone on the test strip, wherein a complementary binding member to the analyte is immobilized. The extent to which the analyte becomes bound in the detection zone can be determined with the aid of the conjugate which can also be incorporated in the test strip or which can be applied separately. In one embodiment, an antibody specific for SDMA is immobilized on a solid support at a distinct location. Following addition of the sample, detection of SDMA-antibody complexes on the solid support can be by any means known in the art. For example, U.S. Pat. No. 5,726,010, which is incorporated herein by reference in its entirety, describes an example of a lateral flow device, the SNAP® immunoassay device (IDEXX Laboratories).

Other detection technologies employ magnetic particles or microbeads, for example, superparamagnetic iron oxide impregnated polymer beads. These beads are associated with, for example, a specific binding partner for the analyte. The beads bind with the target analytes in the sample being tested and are then typically isolated or separated out of solution magnetically. Once isolation has occurred, other testing may be conducted, including observing particular images or labels, whether directly optically or by means of a camera.

In a further embodiments, SDMA analogs, particularly thiol-containing, hydroxyl-containing, amino containing, and carboxylate containing SDMA analogs, enable the SDMA to be linked to another molecule (conjugation target), such as an activated protein, to form an SDMA conjugate. The SDMA analogs described herein enable SDMA to be linked to a conjugation target such as a protein, polypeptide, detectable label, solid support, and the like to provide the SDMA conjugate. The SDMA conjugates described herein can be used to produce antibodies for use in immunoassays specific for SDMA. The antibodies have little or no cross-reactivity with arginine, ADMA, and/or monomethylarginine. The SDMA analogs can also be conjugated to a label for use in immunoassays specific for SDMA.

The SDMA analogs may have, for example, the following structures:

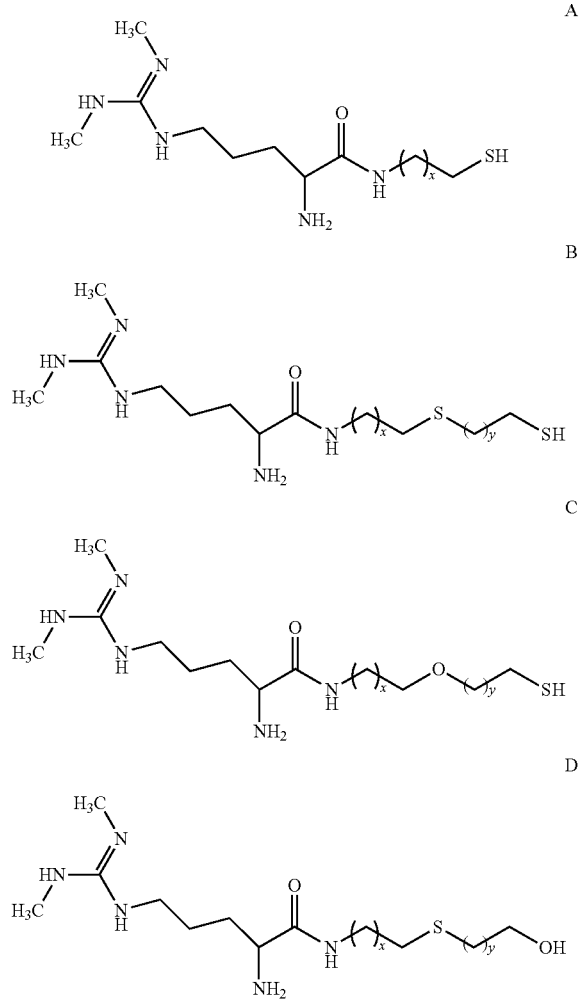

wherein x and y are integers ranging from 1 to 5.

According to one embodiment, the SDMA analogs have the following general formula:

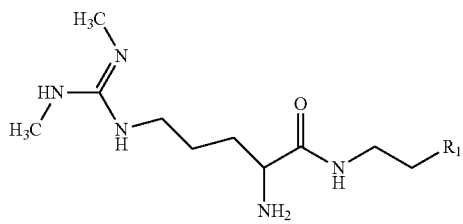

where $R_1$ may be a thiol (or protected thiol), a hydroxyl (or protected hydroxyl), an amino (or protected amino) group, or a carboxylate (including carboxylic acid) or protected carboxylate group.

Suitable thiol, hydroxyl, amino, and carboxylate protecting groups are known to those skilled in the art such as those described, for example, in T. W. Greene, et al. *Protective Groups in Organic Synthesis,* 3rd ed. (1999).

In one particular embodiment, the SDMA analog is a compound of formula (3):

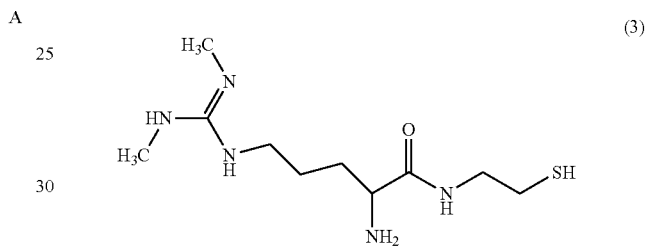

(3)

or a salt thereof. The compound of formula (3) provides an available thiol that can react with a conjugation target that includes an appropriate "thiol-reactive site," i.e., a site that will react with a thiol group. For example, maleimides, alkyl and aryl halides, and alpha-haloacyls are illustrative thiol-reactive sites that can react with thiols to form thio-ethers. Similarly, pyridyl disulfides can react with thiols to form mixed disulfides.

In another embodiment, $R_1$ is X—$R_2$, wherein X is —S—, —O—, —N—, or, —COO— and $R_2$ is a label having a thiol, hydroxyl, amino, or carboxylate reactive group.

In one embodiment, $R_1$ is X—$R_2$, wherein X is —S—, —O—, —N—, or, —COO— and $R_2$ is a protein that has been functionalized to include a thiol, hydroxyl, amino, or carboxylate reactive group.

In one embodiment, SDMA is conjugated to a carrier protein to form a "hapten-carrier" immunogen that can be used to stimulate an immune response to an epitope that includes SDMA. Exemplary immunogenic proteins include, but are not limited to, BSA, KLH, and ovalbumin. Protocols for conjugating haptens to immunogenic proteins are known in the art (see, e.g., Antibodies: A Laboratory Manual, E. Harlow and D. Lane, eds., Cold Spring Harbor Laboratory (Cold Spring Harbor, N.Y., 1988) pp. 78-87).

In one embodiment, the SDMA analog is conjugated to a maleimide activated protein, such as, for example, maleimide activated keyhole limpet protein (KLH) or maleimide activated bovine serum albumin (BSA).

In one embodiment, the compound of formula (3) is conjugated to a maleimide activated protein, such as, for example, maleimide activated keyhole limpet protein (KLH) or maleimide activated bovine serum albumin (BSA).

Thus, in a specific embodiment, a conjugate of a compound of formula (3) and maleimide activated protein has the formula:

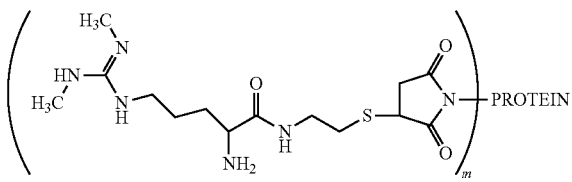

wherein m is an integer.

Typically, m is greater than 5. However, the value for m is variable. For example, m is about 15 maleimide groups per protein in maleimide activated BSA commercially available from Sigma-Aldrich of St. Louis, Mo.; m is about 80 maleimide groups per protein in maleimide activated KLH commercially available from Sigma-Aldrich; m is in a range of about 15 to about 25 maleimide groups per protein in maleimide activated BSA commercially available from Thermo Scientific Pierce Protein Research Products of Rockford, Ill.; m is greater than about 400 maleimide groups per protein in maleimide activated KLH commercially available from Thermo Scientific Pierce Protein Research Products; and m is in a range of about 150 to about 300 maleimide groups per protein in maleimide activated KLH commercially available from A. G. Scientific of San Diego, Calif. In general, m is limited by the number of available amine groups present in an immunogenic protein. The number of available amines can be increased by conjugating the immunogenic protein to polyamines.

In one embodiment, PROTEIN is BSA and m is greater than about 5. In one embodiment, PROTEIN is BSA and m is greater than about 10. In one embodiment, PROTEIN is BSA and m is greater than about 25. In one embodiment, PROTEIN is BSA and m is greater than about 50. In one embodiment, PROTEIN is BSA and m is greater than about 75. In one embodiment, PROTEIN is BSA and m is in a range of about 5 to about 80. In one embodiment, PROTEIN is BSA and m is greater than about 75. In one embodiment, PROTEIN is BSA and m is in a range of about 10 to about 80. In one embodiment, PROTEIN is BSA and m is greater than about 75. In one embodiment, PROTEIN is BSA and m is in a range of about 20 to about 80. In one embodiment, PROTEIN is BSA and m is greater than about 75. In one embodiment, PROTEIN is BSA and m is in a range of about 30 to about 80.

In one embodiment, PROTEIN is KLH and m is greater than about 5. In one embodiment, PROTEIN is KLH and m is greater than about 50. In one embodiment, PROTEIN is KLH and m is greater than about 100. In one embodiment, PROTEIN is KLH and m is greater than about 200. In one embodiment, PROTEIN is KLH and m is greater than about 300. In one embodiment, PROTEIN is KLH and m is greater than about 400. In one embodiment, PROTEIN is KLH and m is greater than about 500. In one embodiment, PROTEIN is KLH and m is greater than about 600. In one embodiment, PROTEIN is KLH and m is greater than about 700. In one embodiment, PROTEIN is KLH and m is greater than about 800. In one embodiment, PROTEIN is KLH and m is in a range of about 5 to about 800. In one embodiment, PROTEIN is KLH and m in a range of about 5 to about 600. In one embodiment, PROTEIN is KLH and m in a range of about 5 to about 400. In one embodiment, PROTEIN is KLH and m in a range of about 5 to about 200. In one embodiment, PROTEIN is KLH and m in a range of about 5 to about 100. In one embodiment, PROTEIN is KLH and m in a range of about 100 to about 200. In one embodiment, PROTEIN is KLH and m ranges in a range of 100 to about 300. In one embodiment, PROTEIN is KLH and m in a range of about 100 to about 400. In various aspects, PROTEIN is KLH and m in a range of about 100 to about 500, about 100 to about 600, about 100 to about 700, about 100 to about 800, or about 100 to about 1,000.

The conjugate of a compound of formula (3) and maleimide activated protein can be characterized using methods well known to those skilled in the art (see, for example, Sigma-Aldrich Technical Bulletin for Maleimide Activated BSA, KLH Conjugation Kit (catalog no. MBK1)).

In an alternate embodiment, the SDMA analog is linked to a detectable label through the thiol, hydroxyl, amino, or carboxylate group. The label may be detectable by itself (e.g., radioisotope labels, chemiluminescent dye, electrochemical labels, metal chelates, latex particles, or fluorescent labels) or, in the case of an enzymatic label, may catalyze chemical alteration of a substrate compound or composition which is detectable (e.g., enzymes such as horseradish peroxidase, alkaline phosphatase, and the like). The label may be a specific binding molecule which itself may be detectable (e.g., biotin, avidin, streptavidin, digoxigenin, maltose, oligohistidine, 2, 4-dinitrobenzene, phenylarsenate, ssDNA, dsDNA, etc.). The SDMA can be linked to a detectable label using methods well known to those skilled in the art. As an illustrative example, the SDMA analog can be linked to maleimide activated peroxidase, from horseradish lyophilized powder, greater than about 200 units/mg protein (commercially available from Sigma-Aldrich St. Louis, Mo. (catalog no. P1709) following the directions in the product manual).

The analog of formula (3) may be prepared from SDMA (commercially available from EMD Chemicals Inc. of Gibbstown, N.J.) by the following illustrative synthetic scheme (1):

Scheme 1

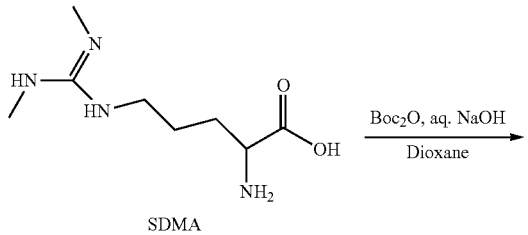

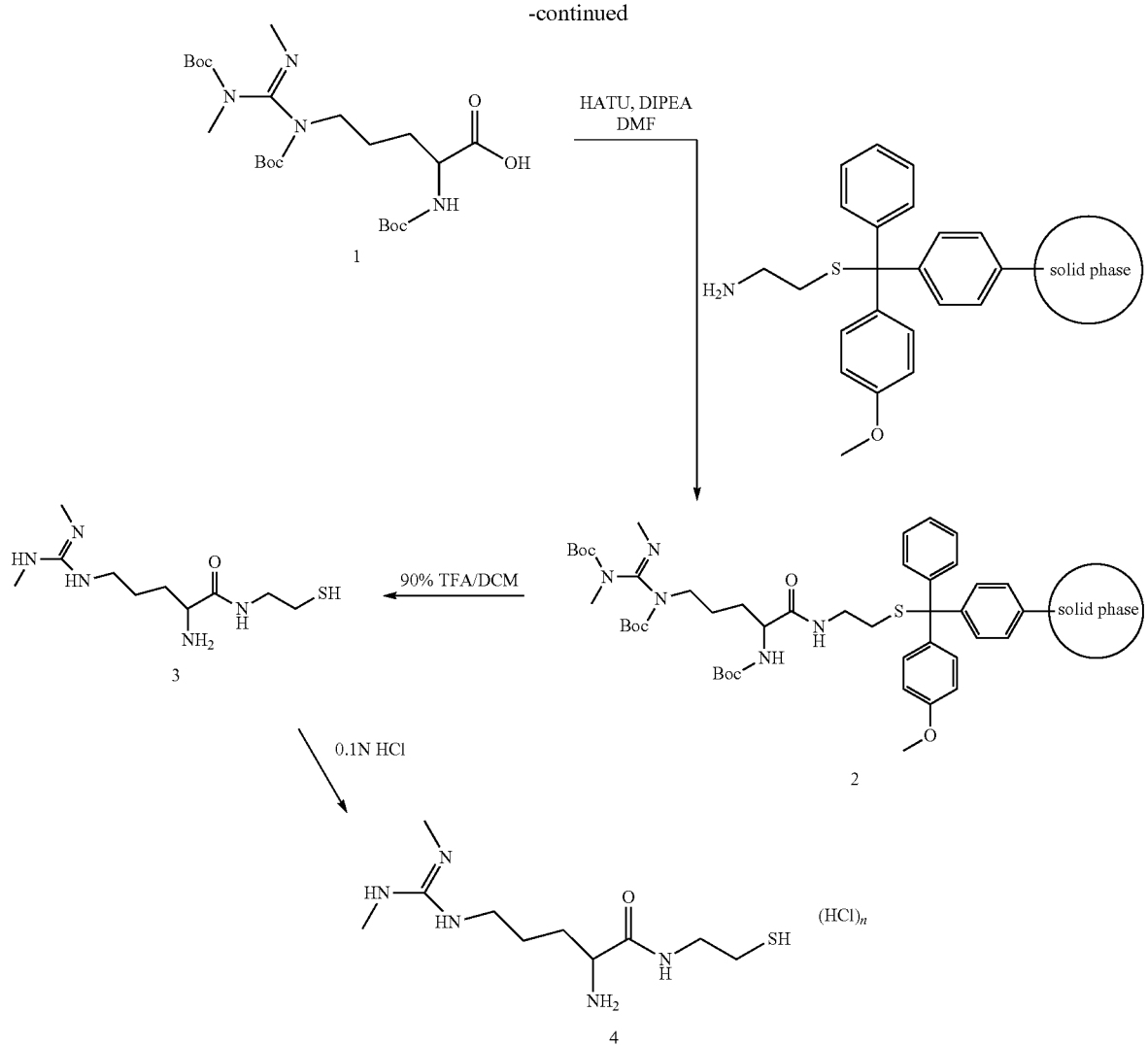

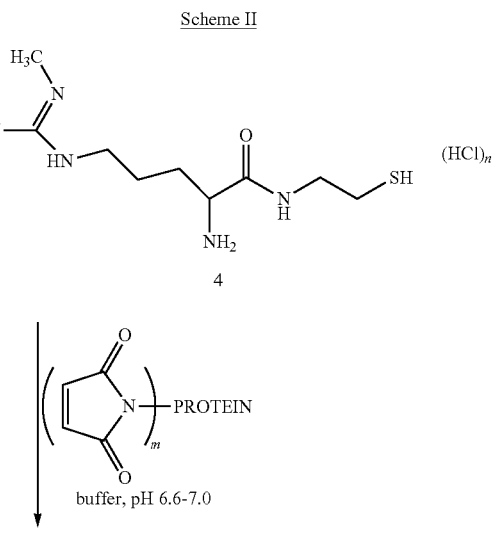

Scheme II

The primary and secondary amino groups of SDMA are protected by reacting SDMA with di-tert-butyldicarbonate (Boc$_2$O). The resulting tert-butoxycarbonyl (BOC) protected SDMA ((Boc$_3$)-SDMA, 1) is then linked to a resin. For example, the (Boc$_3$)-SDMA (1) can be linked to a cysteamine-4-methoxy trityl resin (commercially available from EMD Chemicals, Inc. of Gibbstown, N.J.) by contacting the (Boc$_3$)-SDMA (1) with the resin in the presence of 2-(1H-7-azabenzotriazol-1-yl)-1,1,3,3-tetramethyl uranium hexafluorophosphate methanamininium (HATU) and N,N-diisopropylethylamine (DIPEA) in dimethyl formamide (DMF) to provide resin bound (Boc$_3$)-SDMA cystamide (2). The BOC protecting groups on the resin bound (Boc$_3$)-SDMA cystamide (2) are removed and the resulting resin bound SDMA cystamide cleaved from the resin using, for example, trifluoroacetic acid in dichloromethane, to provide SDMA cystamide (3), which was converted to the hydrochloride salt (4) by reaction with hydrochloric acid.

The analogs of formula A-D, described above, can be made using similar methodologies as described in Scheme 1.

Maleimide activated protein can then be reacted with SDMA cystamide (3) to provide a SDMA cystamide protein conjugate as described below in Scheme II:

-continued

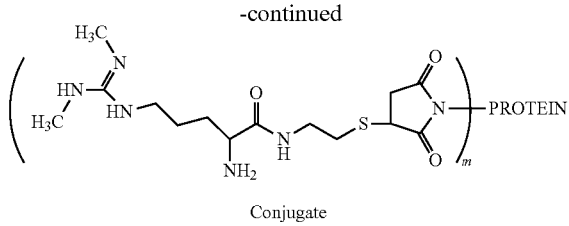

Conjugate wherein n is an integer ranging from 1 to 3 and m is an integer as defined above.

The resulting conjugate can be purified using methods known to those skilled in the art including, but not limited to column chromatography, for example, using gel-filtration column chromatography with Sephadex (for example, Sephadex G-25M) as the solid support (commercially available from Sigma-Aldrich).

Conjugates of analogs A-D can be made using similar methodologies as described in Scheme 2.

The conjugate of the analog of formula A-D and maleimide activated KLH or maleimide activated BSA may be used as an immunogen to generate antibodies that substantially bind SDMA (i.e., anti-SDMA antibodies) and show no or substantially no cross reactivity with ADMA, L-arginine, and/or N-methylarginine. The conjugate of the analog of formula (3) and maleimide activated KLH or maleimide activated BSA may be used as an immunogen to generate antibodies that substantially bind SDMA (i.e., anti-SDMA antibodies). Such antibodies show no or substantially no cross reactivity with ADMA, L-arginine, and/or N-methylarginine.

Anti-SDMA antibodies useful in the methods, devices and kits of the disclosure are characterized by a high affinity binding to SDMA with little or no cross-reactivity to ADMA, arginine, and/or monomethylarginine. Accordingly, described herein are isolated, recombinant, synthetic, and/or in vivo-produced anti-SDMA antibodies, as well as methods of making and using such antibodies, including diagnostic and therapeutic compositions, methods, and devices. The anti-SDMA antibodies described herein are useful, for example, as a diagnostic marker for renal function, such as kidney impairment, renal insufficiency, glomerular filtration rate (GFR), inulin clearance, and creatinine clearance, and for renal disorders/diseases, such as chronic kidney disease, glomerulonephritis, diabetic nephropathy, interstitial nephritis, polycystic kidney disease, and hypertensive kidney disease.

In one embodiment, the generated antibodies are able to detect free SDMA (i.e., SDMA not part of a polypeptide chain) and show no or substantially no cross-reactivity with ADMA, L-arginine, and/or N-methylarginine. As shown in the Examples, antibodies described herein show less than 1% cross reactivity with ADMA, L-arginine and/or N-methylarginine, based on equal concentrations of the antigens. As generally understood in the art, the impact of cross-reactivity will depend on the relative abundance of the cross-reacting antigen (e.g., ADMA, L-arginine and/or N-methylarginine) as compared to the immunizing antigen (SDMA) in a test sample. For example, a cross-reactivity as high as 50% may be acceptable if the concentration of the immunizing antigen is 100-fold greater than that of the cross-reacting antigen. Conversely, a cross-reactivity as low as 1% may be problematic if the concentration of the cross-reacting antigen is 100-times that of the immunizing antigen. Accordingly, the impact of cross-reactivity must be considered in context of the relative abundances of any cross-reacting antigens and the immunizing antigen, in the sample to be analyzed. In the various aspects of the disclosure, cross reactivity does not affect the substantial binding of SDMA or SDMA analog to an anti-SDMA antibody.

The methods for making the antibodies may include using one or more SDMA conjugates as an immunogen to stimulate an immune response. The methods include administering one or more SDMA conjugates to an animal using a suitable immunization protocol, and separating an appropriate antibody from a body fluid(s) of the animal, as described, for example, in Example 3, infra. Alternatively, the SDMA conjugates may be used in phage display methods to select phage displaying on their surface an appropriate antibody, followed by separation of nucleic acid sequences encoding at least a variable domain region of an appropriate antibody. Phage display methods are well known to those of ordinary skill in the art. (See, for example, Antibody Phage Display; Methods in Molecular Biology, Vol. 178, O'Brien, Philippa M.; Aitken, Robert (Eds.) 2002). Monoclonal antibodies to SDMA can be prepared by methods generally known in the art.

The SDMA analogs described herein may be linked to a label to provide a detectable conjugate for use in receptor binding assays, such as immunoassays for SDMA. Similarly, the anti-SDMA antibodies can be linked to a label to provide detectable anti-SDMA antibodies for use in receptor binding assays, such as immunoassays for SDMA. The SDMA analogs and anti-SDMA-antibodies can be linked to a label using methods well known to those skilled in the art. E.g., Immunochemical Protocols; Methods in Molecular Biology, Vol. 295, edited by R. Burns (2005)). The detectable SDMA conjugate or detectable anti-SDMA antibodies may be used in various homogenous, sandwiches, competitive, or non-competitive assay formats, to generate a signal that is related to the presence or amount of an SDMA in a test sample.

In a specific embodiment, the immunoassay methodologies are competitive immunoassays for detection of anti-SDMA antibodies. The competitive immunoassay may be carried out in the following illustrative manner. A sample, from an animal's body fluid, potentially containing anti-SDMA antibodies, is contacted with an SDMA analog conjugated to a solid support and with an anti-SDMA antibody conjugated to a detectable label. The anti-SDMA antibodies of interest, present in the sample, compete with the anti-SDMA antibody conjugated to a detectable label for binding with the SDMA analog conjugated to a solid support. The amount of the label associated with the solid support can be determined after separating unbound antibodies and the solid support. In an alternative embodiment, the competitive immunoassay is carried out in the following illustrative manner. A sample, from an animal's body fluid, potentially containing anti-SDMA antibodies, is contacted with an SDMA analog linked to a detectable label and then with an antibody conjugated to a solid support. The anti-SDMA antibodies in the sample compete with the anti-SDMA antibodies on the solid support for binding with the SDMA conjugate linked to a detectable label. In either case, the signal obtained is inversely related to the amount of SDMA antibody of interest present in the sample.

Figure 2:
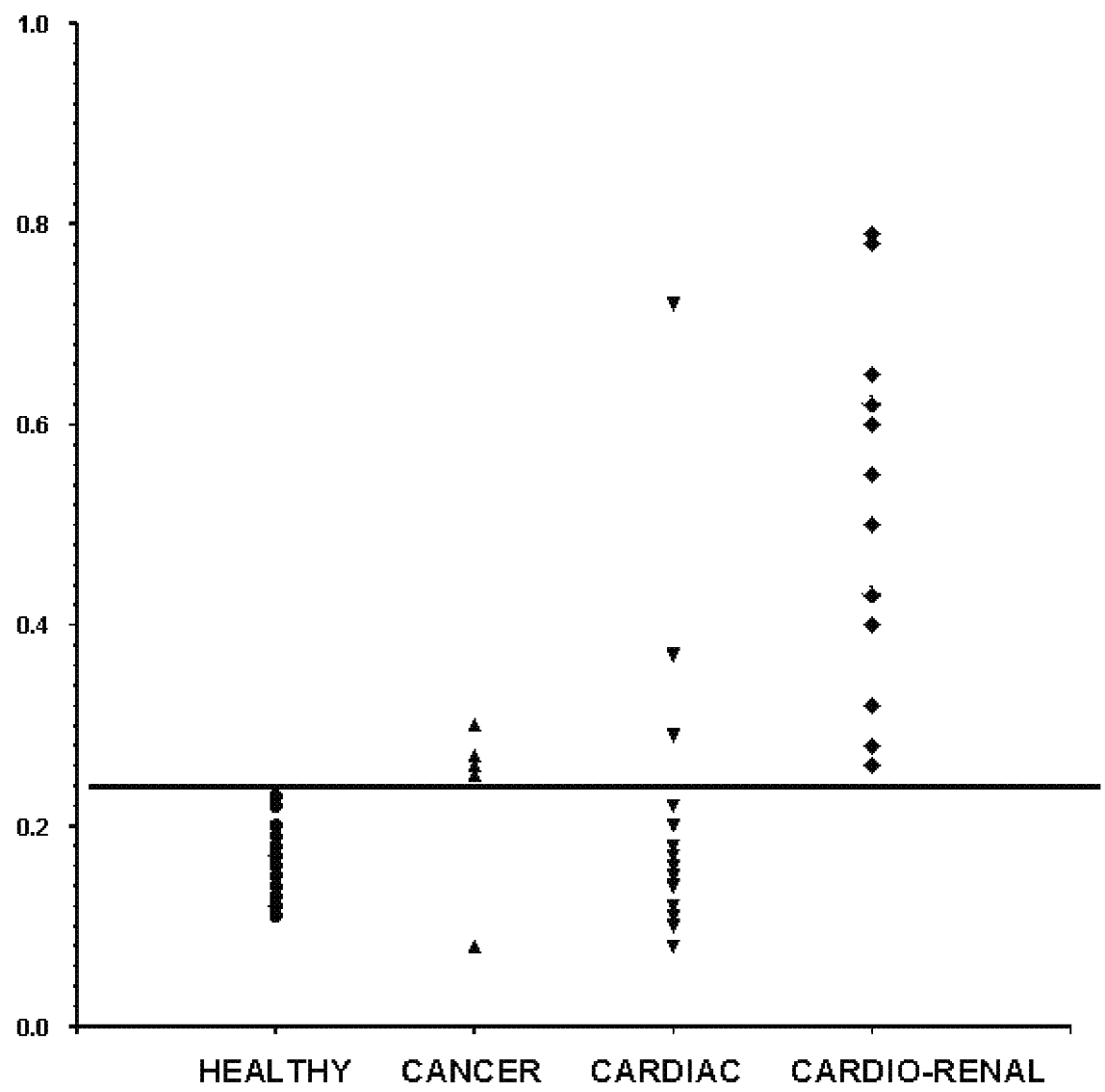
FIG. 2 is a plot of SDMA concentrations in healthy dogs and dogs having cancer, cardiac disease, or cardio-renal disease. The horizontal bar represents the cutoff value (determined as mean SDMA concentration plus 2 standard deviations from a population of healthy dogs).
Figure 3:
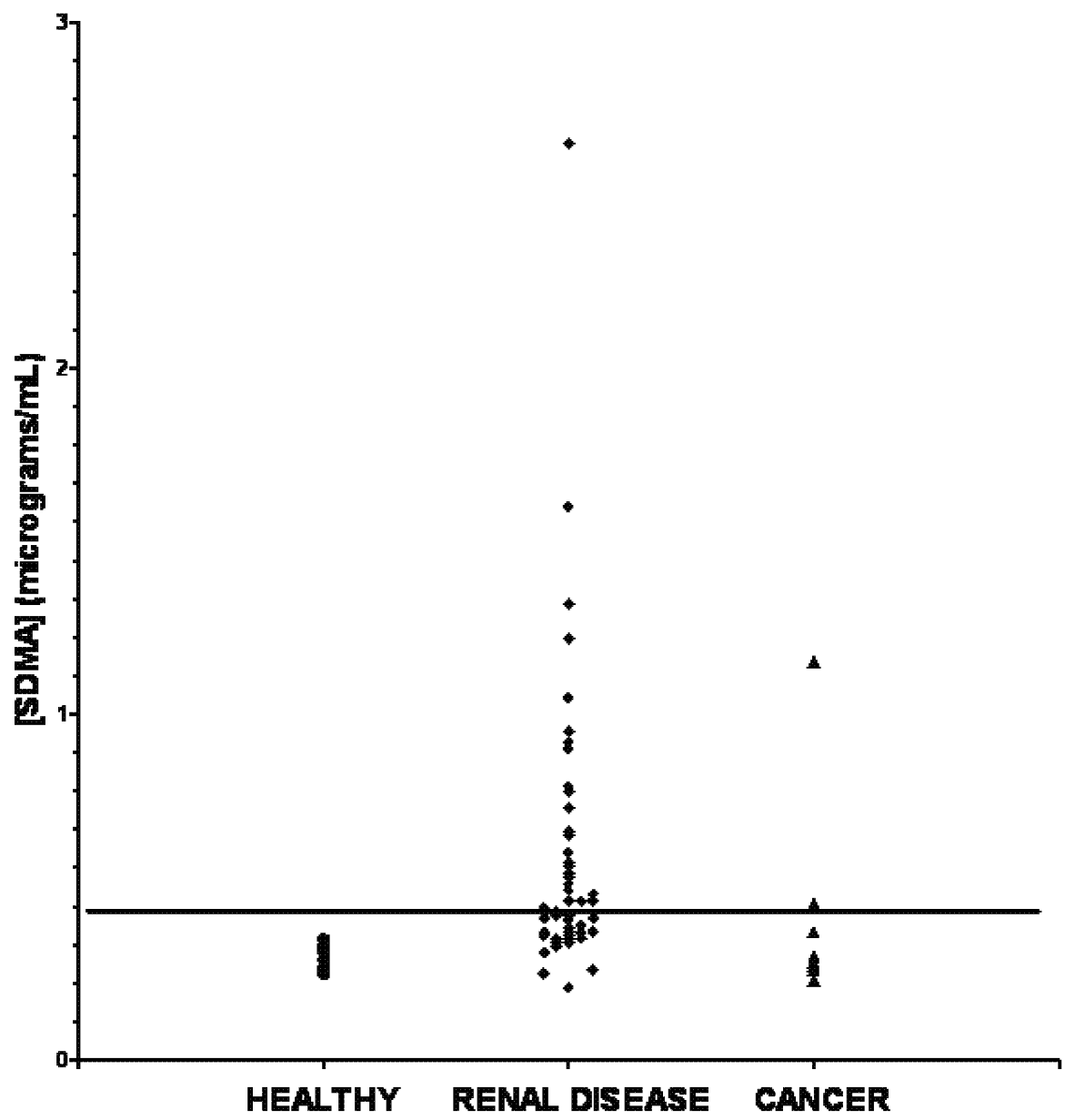
FIG. 3 is a plot of SDMA concentrations in healthy cats and cats having renal disease or cancer. The horizontal bar represents the cutoff value (determined as mean SDMA concentration plus 2 standard deviations from a population of healthy cats).

Of course, other methods of measuring free SDMA can be used in the methods described herein. SDMA itself can be predictive of disease (see FIGS. 2 and 3).

The concentration of creatinine in serum can be measured in a variety of ways, as is known by the person of skill in the art. For example, a Catalyst Dx™ Chemistry Analyzer or a VetTest® Chemistry Analyzer can be used with dry-slides adapted to test for creatinine, for example, those commercially available from IDEXX Laboratories. Other analyzers and slides, such as the VITROS® 950 analyzer and VITROS® CREA slides available from Ortho Clinical Diagnostics, can also be used. Enzymatic wet assays can also be used. For example, the person of skill in the art can use an enzymatic wet chemistry method on an Integra 800 analyzer. One particular assay is based on a creatininase/creatinase/sarcosine oxidase system with detection at 552 nm and absorbance blanking at 659 nm. The person of skill in the art can also use colorimetric methods, for example, those based on picrate such as the Jaffe assay. Other methods known to the person of skill in the art, such as those described in U.S. Patent Publication no. 2005/0266574 and U.S. Pat. No. 4,818,703, each of which is incorporated herein by reference, can also be used to measure creatinine concentration. In certain embodiments, the measurement of creatinine concentration is performed using isotope dilution mass spectrometry.

Several methods of determining GFR are known. For example, GFR can be determined as the renal clearance of $^{125}$I-iothalamate, as described in Perrone et al., Am. J. Kidney Disease, vol. 16, pp 224-35 (1990) and Levey et al., J. Am. Soc. Nephrol., vol. 4, pp. 1159-71 (1993), each of which is hereby incorporated by reference in its entirety. Other urine collection-based methods can also be used, including measuring the renal clearance of other exogenous substances, e.g. $^{51}$Cr-EDTA, $^{99}$Tc-DTPA, iohexol, or inulin. GFR values obtained by any of these methods can be correlated with the inverse product of the concentrations of creatinine and free SDMA for samples collected at about the same time in order to provide a calibration curve or standard values for use in the methods described herein.

The following are provided for exemplification purposes only and are not intended to limit the scope of the invention described in broad terms above. All references cited in this disclosure are incorporated herein by reference.

EXAMPLES

Example 1

Synthesis of the SDMA Cystamide (3) and SDMA Cystamide Hydrochloride Salt (4)

SDMA cystamide (3) was prepared according to the route of synthesis described in Scheme 1.

(BOC)$_3$-SDMA (1): To a solution of 4.36 g (20 mmol) di-tert-butyldicarbonate (Boc$_2$O) in 20 mL dioxane was added dropwise 550 mg (2.0 mmol) of N, N-dimethylarginine dihydrochloride (SDMA) (commercially available from EMD Chemicals Inc. of Gibbstown, N.J.) dissolved in 10 mL of 5.0 N NaOH over 30 minutes at room temperature with stirring. The resulting reaction mixture was stirred overnight. 30 mL of dichloromethane (DCM) and 30 mL of water were then added to the reaction mixture and the pH adjusted to 6.5 with acetic acid (AcOH). The DCM layer was separated, washed with brine, and dried over anhydrous Na$_2$SO$_4$. The DCM was then removed under reduced pressure to provide a solid. The resulting solid was washed 2 times with 10 mL of hexane. The solid was then dried under vacuum to provide 800 mg of a light yellow solid. Subsequent reactions did not require further purification. The solid was characterized by mass spectroscopy. ESI-MS: 525.7 (M+Na)$^+$, 503.6 (M+1)$^+$, 403.5 (M−Boc+1)$^+$, 303.5 (M−2Boc+1)$^+$.

(Boc)$_3$-SDMA-cystamine-resin (2): To a mixture of 600 mg (1.2 mmol) (Boc)$_3$-SDMA (1) and 627 mg (1.6 mmol) 2-(1H-7-Azabenzotriazol-1-yl)-1,1,3,3-tetramethyl uronium hexafluorophosphate methanaminium (HATU) in 15 mL of dimethylformamide (DMF) was added 420 μL (2.4 mmol) of N,N-diisopropylethylamine (DIPEA). The resulting mixture was then stirred for 20 minutes under a dry N2 atmosphere. Separately, cystamine 4-methoxy trityl resin (1.0 g) (commercially available from EMD Chemicals, Inc. of Gibbstown, N.J.) was swelled and washed using DMF. The swelled resin was then added to the reaction mixture and the reaction mixture gently shaken under a N2 atmosphere for three hours. The resin was then collected by filtration, and washed consecutively with 5 mL of DMF, 5 mL of methanol, and 5 mL of DCM.

SDMA-cystamide (3): To the modified resin was added 15 mL of 90% trifluoroacetic acid (TFA), the resulting mixture gently shaken for two hours, and filtered. The resin was washed twice with 3 mL of TFA/DCM (1:1 (v/v)). The filtrate and washings were combined and added to 200 mL of cold ether to provide a precipitate. The resulting precipitate was collected by centrifugation and dried under reduced pressure to provide 300 mg of SDMA-cystamide (3). The SDMA-cystamide (3) was characterized by mass spectroscopy. EIS-MS: 262.4 (M+1)+, 132.0 (M+2)+.

SDMA-cystamide hydrochloride salt (4): SDMA-cystamide 3 (300 mg) was reconstituted in 5 mL of 1.0 N HCl and the resulting mixture was lyophilized to provide a light yellow solid as a foam.

The same general procedure as described above can be used to prepare other SDMA analogs.

Example 2

Conjugation of SDMA Cystamide (3) With Maleimide Activated Protein

A. General procedure for conjugating SDMA cystamide (3) with maleimide activated KLH:
1. Slowly opened a vial of maleimide activated KLH (commercially available from Sigma-Aldrich St. Louis, Mo. (catalog no. K0383)) to release the vacuum.
2. Reconstituted the contents of the vial with 1 mL of water to provide a 5 mg/mL solution of maleimide activated KLH in 20 mM sodium phosphate buffer with 230 mM NaCl, 2 mM EDTA, and 80 mM sucrose, pH 6.6.
3. Prepared a conjugation buffer solution of 20 mM sodium phosphate buffer with 100 mM EDTA and 80 mM sucrose, pH 6.6 by reconstituting conjugation buffer (commercially available from Sigma-Aldrich St. Louis, Mo. (catalog no. C3957)) with 10 mL of water.
4. Dissolved approximately 0.8 mg of hapten (i.e., SDMA cystamide (3)) in 0.5 mL of conjugation buffer. Retained 50 μl of the resulting peptide solution for determination of coupling efficiency (hap-total). The retained hapten solution was stored at 2-8° C.
5. The hapten solution of step 4 was immediately mixed with the maleimide activated KLH solution of step 2 in a reaction vial equipped with stirring bar. The resulting mixture was de-gassed while stirring under a gentle nitrogen stream for about 1-2 minutes.
6. The reaction vial was capped and stirring continued at room temperature for 2 hours or overnight at 2-8° C.
7. 100 μl of the conjugation reaction from step 6 (hap-free) was retained for determination of coupling efficiency.

B: General procedure for conjugating SDMA cystamide (3) with maleimide activated BSA:
1. Slowly opened a vial of maleimide activated BSA (commercially available from Sigma-Aldrich St. Louis, Mo. (catalog no. B7542)) to release the vacuum.
2. Reconstituted the contents of the vial with 1 mL of water to provide a 5 mg/mL solution of maleimide activated BSA in 20 mM sodium phosphate buffer with 230 mM NaCl, 2 mM EDTA, and 80 mM sucrose, pH 6.6.
3. Dissolved 5 mg of hapten (i.e., SDMA cystamide (3)) in 0.5 mL of conjugation buffer (prepared as described above in step A3). Retained 50 µl of the resulting peptide solution for determination of coupling efficiency (hap-total). The retained hapten solution was stored at 2-8° C.
4. The hapten solution of step 3 was immediately mixed with the maleimide activated BSA solution of step 2 in a reaction vial equipped with stirring bar. The resulting mixture was de-gassed while stirring under a gentle nitrogen stream for about 1-2 minutes.
5. The reaction vial was capped and stirring continued at room temperature for 2 hours or overnight at 2-8° C.
6. 100 µl of the conjugation reaction from step 5 (hap-free) was retained for determination of coupling efficiency.

Figure 4:
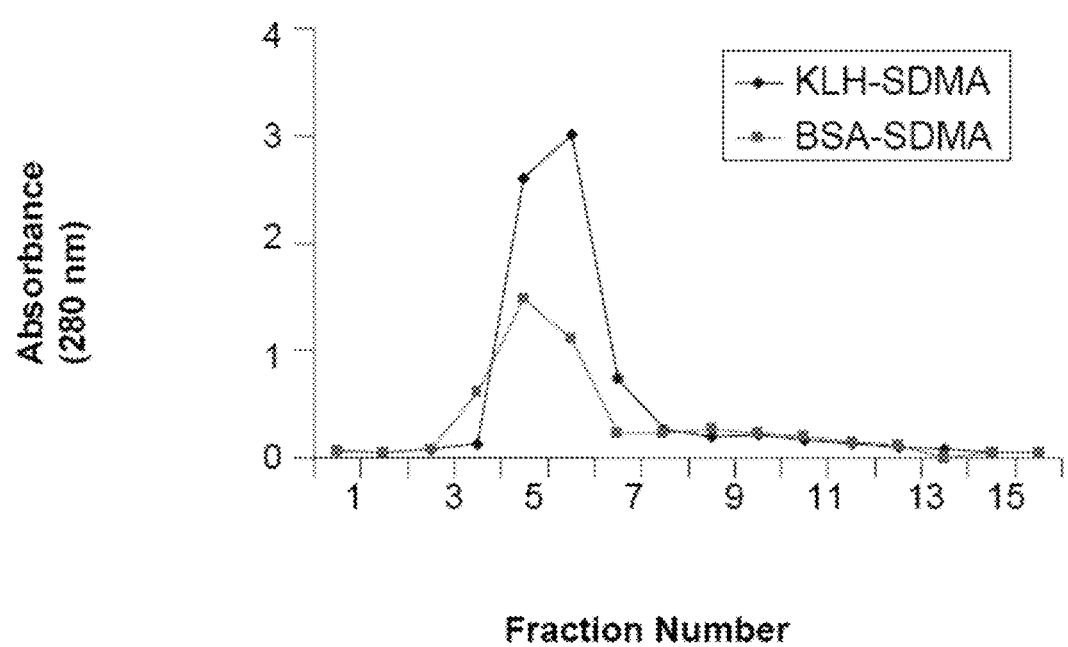
FIG. 4 is a plot of absorbance at 280 nm v. fraction number for elution of an SDMA cystamide protein conjugate, wherein the protein is KLH (♦) or BSA (■), from a Sephadex G-25M gel-filtration column as described in the Examples.

C: Isolation of KLH or BSA conjugates:
1. Dissolved the contents of a phosphate buffered saline package (PBS) package (commercially available from Sigma-Aldrich St. Louis, Mo. (catalog no. P3813)) in 1 liter of water.
2. Supported a Sephadex G-25M gel filtration column (commercially available from Sigma-Aldrich St. Louis, Mo. (catalog no. B4783)) over a beaker.
3. Removed the cap from the top of the column, cut open lower tip of column, and let excess of liquid flow through. Did not allow the column to run dry.
4. Equilibrated the column with 30 mL of PBS.
5. The reaction mixture from Example 2A or 2B was applied to the column.
6. The column was eluted with PBS, using a total volume of about 10 mL and fractions of about 0.5-1.0 mL were collected. The presence of protein in the fractions was monitored by measuring the absorbance of each fraction at 280 nm.
7. The fractions containing protein were combined. FIG. 4 graphically depicts absorption v. fraction number of an illustrative elution profile for the proteins KLH (♦) and BSA (■).
8. The fractions containing protein were divided into small aliquots that were stored frozen at −20° C.

D. Assay to determine coupling efficiency:
1. Cysteine Standard Assay—To estimate the coupling efficiency of the analog to the cysteine peptide, a standard curve was prepared using known concentrations of cysteine. The assay was based on the reaction of 5,5'-dithiobis(2-nitrobenzoic acid) (DTNB or Ellman's reagent) which reacts with sulfhydryl groups at pH 8.0 to produce a chromophore with maximum absorption at 412 nm. The following procedure was followed:
   a. A DTNB buffer was prepared by dissolving the contents of the vial of the DTNB buffer (commercially available from Sigma-Aldrich St. Louis, Mo. (catalog no. D4179)) in 10 mL of water.
   b. DTNB reagent (commercially available from Sigma-Aldrich St. Louis, Mo. (catalog no. D8130)) was then dissolved in 5 mL of the DTNB buffer from step a.
   c. Immediately before use, a cysteine solution was prepared by dissolving 32 mg of L-cysteine hydrochloride monohydrate (commercially available from Sigma-Aldrich St. Louis, Mo. (catalog no. C7880)) in 1 mL of water. The resulting solution of L-cysteine hydrochloride was serially diluted with water to provide diluted stock solutions in the range of 0.4-0.04 mg/mL. The diluted stock solutions were used immediately.
   d. To labeled test tubes was added 50 µL of the diluted stock solutions. A test tube containing 50 µL of water was used as a blank.
   e. To each test tube was then added 0.1 mL of water, 0.75 mL of DTNB buffer, pH 8.0, and, immediately, 0.1 mL of DTNB reagent solution (1 mg/mL) to provide a final cysteine standard assay solution with a volume of 1 mL.
   f. Mixed contents of each test tube.
   g. The absorbance of each cysteine standard assay solution was determined at 412 nm. If the absorbance was above 1.4, the samples were diluted and the assay repeated.
   h. Absorbance at 412 nm was plotted against cysteine concentration (mg/mL) to provide a standard curve. The linear part of the standard curve, with cysteine concentrations ranging from 2-20m/ml, was used for determining hap-total and hap-free.

2. Hapten Assay—Note: If samples generated values higher than the highest cysteine standard in the cysteine standard assay, the samples were diluted and the assay repeated.
   a. To appropriately labeled test tubes was added 50 µl of the following solutions to:
      (i) DTNB Buffer (Blank)
      (ii) Diluted peptide sample (hap-total, from KLH conjugation, from step A4 of Example 2)
      (iii) hapten-KLH (hap-free, from KLH conjugation step A7 of Example 2)
      (iv) Diluted peptide sample (hap-total, from BSA conjugation step B3 of Example 2)
      (v) hap-BSA (hap-free, from BSA conjugation, step B6 of Example 2)
   b. To each labeled tube from step (a) was added 0.1 mL of water, 0.75 mL of DTNB buffer, pH 8.0, and, immediately, 0.1 ml of DTNB reagent solution (1 mg/mL), to provide a final hapten assay solution with a volume of 1 mL.
   c. Mixed the contents of each tube.
   d. The absorbance of the solution in each labeled tube was determined at 412 nm. If the absorbance was above 1.4, the samples are diluted and the assay repeated.
   e. The concentration of hap-total was then determined from the measured absorbance using the standard curve obtained as described above in section 1h. The absorbance measured for tube (ii) and tube (iv) were used to determine hap-total for KLH and BSA, respectively. The absorbance measured for tube (iii) and tube (v) were used to determine hap-free for KLH and BSA, respectively. The peptide concentration in the undiluted solution and coupling efficiency were then calculated as described under calculations.

3. Calculations
To estimate the peptide concentrations and coupling efficiency, a standard curve was prepared using known concentrations of cysteine as described above (Cysteine Standard Assay). In this calculation, one mole of cysteine is equivalent to one mole of sulfhydryl containing hapten.

The following formulas were used:

% Coupling Efficiency={(Hap(conjugated)/ Hap(total)}×100=[{Hap(total)−Hap(free)}/Hap(total)]×100

Hap(total)=Peptide(total)μmole/ml

Hap(free)=Peptide(free)μmole/ml

Hap(conjugated)=Hap(total)−Hap(free)

(See, also, Sigma-Aldrich Technical Bulletin for Maleimide Activated BSA, KLH Conjugation Kit (catalog no. MBK1)). This same general procedure as described in Examples 2A-D can be used to measure the efficiency of the conjugation of other SDMA analogs to KLH and BSA.

Example 3

Method for Generating Anti-SDMA Antibodies

The immunization protocol for generating the anti-SDMA antibodies was carried out according to the following protocol. Six California breed rabbits were immunized with an SDMA-conjugate. Three of the six rabbits were immunized with SDMA conjugated with BSA (rabbits #155, 156 and 157) and the other three rabbits were immunized with SDMA conjugated with KLH (rabbits #152, 153 and 154) (prepared as described in Example 2). For primary immunizations, each rabbit was injected with 0.5 mg of the SDMA conjugate in 1 ml of phosphate buffered saline (PBS) mixed with 1 ml of Freund's complete adjuvant. Each rabbit received 20-30 intradermal injections on their shaved back. Each rabbit was boosted with 0.25 mg of immunogen in 1 ml PBS mixed with equal volume of Freund's incomplete adjuvant in the hind legs. The boosting shots were given each month after the primary injection. Test bleeds of 5 ml blood were taken from each rabbit 7-10 days after each boost. Production bleeds of 40 ml were taken from each rabbit after the third booster shot, when the antisera titer was greater than about 1:2000. Antiserum titer is the dilution of antiserum that generates the steepest calibration curve for the assay.

Example 4

Characterization of Anti-SDMA Antibodies

In order to assess the specificity of the antibodies obtained by the procedures described in Example 3 above, their reactivity to SDMA, ADMA, L-arginine, and/or N-methylarginine was measured in a competitive ELISA assay (Table 1).

ADMA-2HCl, SDMA-2HCl, N-methylarginine acetate (Sigma, Cat. No. M7033) or L-arginine (Sigma, Cat. No. A5006) were each dissolved in PBS to make stock solutions at 1 mg/ml. From these stock solutions, working solutions at 100 μg/ml, 10 μg/ml and 1 μg/ml were prepared in PBS.

50 μl of the SDMA-HRP conjugate (as described in Example 5 below), 50 μl of ADMA, SDMA, N-methylarginine or L-arginine (at concentrations from 1-100 μg/ml as described above), and 50 μl of rabbit anti-SDMA antibody in serum (1:3000 titer) were sequentially added to an individual well in a 96-well polystyrene microwell plate, precoated with sheep anti-rabbit IgG (commercially available from Beacon Analytical Systems Inc. of Portland, Me.). After a 30 minutes incubation period at room temperature, the wells were washed 4 times with PBST (Phosphate Buffered Saline, 0.05% Tween).

100 μl of 3,3',5,5'-Tetramethylbenzidine (commercially available from Promega Corporation of Madison, Wis.) was subsequently added. Following a 30 minutes incubation period at room temperature, 100 μl of stop solution (1 N HCl) was added and the absorbance was measured at 450 nm using a BioTek ELX 808 (Winooski, Vt.) plate reader. The data was subjected to quantification using Softmax software (Molecular Devices, Sunnyvale, Calif.).

The absorbance values obtained with 0 μg/mL, 1 μg/mL, 10 μg/mL, and 100 μg/mL of ADMA, SDMA, N-methylarginine or L-arginine, respectively, were determined and plotted. The concentration of SDMA at which the absorbance value was reduced by 50% (relative to the maximum absorbance obtained at 0 μg/mL SDMA; i.e. IC50) was divided by each of the concentrations of ADMA, N-methylarginine or L-arginine, respectively, at which the absorbance value was reduced by 50% (IC50). The resulting value was multiplied by 100 to obtain the value "% cross-reactivity". Where an absorbance reduction of <50% was observed at concentrations up to and including 100 ug/mL, a cross-reactivity of <1% was noted (See Table 1).

As shown in Table 1, all 6 rabbit anti-SDMA sera had cross-reactivities of <1% to ADMA, N-methylarginine or L-arginine, respectively.

TABLE 1

|  | IC 50 | % Cross Reactivity |
|---|---|---|
| Rabbit # 152 (1:5K) | | |
| SDMA | 1.10 μg/ml | 100% |
| ADMA | >100 | <1% |
| L-Arginine | >100 | <1% |
| N-MMA | >100 | <1% |
| Rabbit # 153 (1:2.5K) | | |
| SDMA | 0.65 μg/ml | 100% |
| ADMA | >100 | <1% |
| L-Arginine | >100 | <1% |
| N-MMA | >100 | <1% |
| Rabbit # 154 (1.25K) | | |
| SDMA | 0.49 μg//ml | 100% |
| ADMA | >100 | <1% |
| L-Arginine | >100 | <1% |
| N-MMA | >100 | <1% |
| Rabbit # 155 (1:3K) | | |
| SDMA | 0.73 μg/ml | 100% |
| ADMA | >100 | <1% |
| L-Arginine | >100 | <1% |
| N-MMA | 79 μg/ml | <1% |
| Rabbit # 156 (1:20K) | | |
| SDMA | 1.3 μg/ml | 100% |
| ADMA | >100 | <1% |
| L-Arginine | >100 | <1% |
| N-MMA | >100 | <1% |
| Rabbit # 157 (1:15K) | | |
| SDMA | 1.6 μg/ml | 100% |
| ADMA | >100 | <1% |
| L-Arginine | >100 | <1% |
| N-MMA | >100 | <1% |

A similar experiment to that described in Examples 1-4, but wherein ADMA was used rather than SDMA, also generated antibodies. Using an ADMA-protein conjugate to generate antibodies, however, produced antibodies that were not specific to free ADMA and were not useful in an assay to measure ADMA.

In another experiment, using only polyclonal antibody from Rabbit No. 154, the specificity of the antibody was determined with greater stringency by the method described above. This data (see Table 2) shows that that the specificity for antibody from Rabbit No. 154 is even greater than shown in Table 1, above.

TABLE 2

Specificity (Cross-Reactivity) Rabbit No. 154

| | Cross-reactivity |
|---|---|
| SDMA | 100% |
| ADMA | <0.2% |
| Arginine | <0.01% |
| LMMA | <1% |

Example 5

Competitive Immunoassay for Detecting In Vivo SDMA Levels

Serum samples were provided by veterinary clinics/labs from animals that were subjected to a routine physical exam and a routine chemistry panel.

A SDMA-HRP conjugate was prepared according to the following procedure:

1. Maleimide activated horseradish peroxidase lyophilized powder, >200 units/mg protein (commercially available from Sigma-Aldrich St. Louis, Mo. Product no. P1709)) was reconstituted to 2-5 mg/mL in 0.15 M NaCl, 0.1 M sodium phosphate, pH 7.0. The buffer was deaerated and purged with nitrogen or argon before use and the water used to prepare the buffer was free of trace heavy metals and other oxidizing agents. The coupling was performed in an amber vial to protect the reaction from light.
2. SDMA analog (3) was dissolved in the same buffer as used in step 1 to provide a solution with a concentration of 2-5 mg/mL. Generally 1-2-moles of peroxidase per mole sulfhydryl compound were used. The molecular weight of peroxidase is about 40,000.
3. The solution from step 1 was combined with the solution from step 2 and the resulting solution stirred gently for 3 hours at room temperature. Unreacted maleimide groups were then blocked by adding 1M 2-Mercaptoethanol (commercially available from Sigma-Aldrich St. Louis, Mo.(catalog no. M 6250)) to provide a final concentration of 0.0015 M 2-Mercaptoethanol and the resulting solution is stirred for about 15 minutes.
4. Unreacted sulfhydryl groups were then blocked by adding 0.3 M N-ethylmaleimide (commercially available from Sigma-Aldrich St. Louis, Mo. (catalog no. D 8654)) to the solution from step 3 to provide a final concentration of 0.003 M N-ethylmaleimide.
5. The resulting solution of the SDMA-HRP conjugate was then exchanged into PBS by chromatography (using the same procedure described above in the Example for conjugating SDMA analog (3) to maleimide activated KLH and BSA) or dialysis into PBS (Spectra/Por3, MWCO 3500 Spectrum Labs, Rancho Dominguez, Calif.) according to the instructions from the manufacturer. The resulting solution was then lyophilized.

See, also, Lin, F. T., et al., Biochemistry, 18(4), 690 (1979); Kitagawa, T., et al., Chem. Pharm. Bull., 29(4), 1131 (1981); Duncan, R. J. S., et al., Anal. Biochem., 132, 68 (1983); and Palmer, J. L., et al., J. Biol. Chem., 238(7), 2393 (1963).

50 µl of the SDMA-HRP conjugate, 50 µl of serum sample (or calibrator, SDMA 2 HCl, commercially available from Calbiochem of San Diego, Calif.), and 50 µl of rabbit anti-SDMA antibody in serum (1:3000 titer) were sequentially added to an individual well in a 96-well polystyrene microwell plate, precoated with sheep anti-rabbit IgG (commercially available from Beacon Analytical Systems Inc. of Portland, Me.). After a 30 minutes incubation period at room temperature, the wells were washed 4 times with PBST (Phosphate Buffered Saline, 0.05% Tween).

100 µl of 3,3',5,5'-Tetramethylbenzidine (commercially available from Promega Corporation of Madison, Wis.) was subsequently added. Following a 30 minutes incubation period at room temperature, 100 µl of stop solution (1 N HCl) was added and the absorbance was measured at 450 nm using a BioTek ELX 808 (Winooski, Vt.) plate reader. The data was subjected to quantification using Softmax software (Molecular Devices, Sunnyvale, Calif.). A calibration curve was generated by running a series of SDMA standards (e.g., 0, 0.05 µg/mL, 0.15 µg/mL, 0.45 µg/mL, and 1.35 µg/mL). The unknown samples were quantified using the calibration curve. The results are summarized in Table 3.

TABLE 3

| Species | Status | SDMA µM |
|---|---|---|
| Canine | Healthy | 1.1 |
| Canine | Healthy | 1.1 |
| Canine | Healthy | 1.1 |
| Canine | Healthy | 0.7 |
| Canine | Healthy | 1.7 |
| Canine | Healthy | 1.4 |
| Canine | Healthy | 1.2 |
| Canine | Healthy | 1.7 |
| Canine | Healthy | 1.9 |
| Canine | Renal Disease | 13.3 |
| Canine | Renal Disease | 6.1 |
| Canine | Renal Disease | 2.8 |
| Canine | Renal Disease | 2.2 |
| Canine | Renal Disease | 3.5 |
| Canine | Renal Disease | 2.3 |
| Canine | Renal Disease | 1.8 |
| Feline | Healthy | 2.7 |
| Feline | Healthy | 2.9 |
| Feline | Healthy | 3.0 |
| Feline | Healthy | 2.7 |
| Feline | Healthy | 2.5 |
| Feline | Healthy | 2.2 |
| Feline | Healthy | 2.1 |
| Feline | Healthy | 1.9 |
| Feline | Renal Disease | 70.3 |
| Feline | Renal Disease | 6.0 |
| Feline | Renal Disease | 5.2 |
| Feline | Renal Disease | 3.9 |

In Table 3, the status "Renal Disease" indicates that the sample taken from the animal showed creatinine and blood urea nitrogen (BUN) values above the normal reference range and the status "Healthy" indicates that the sample taken from the animal showed normal (reference range) creatinine and blood urea nitrogen (BUN) values. For canines, the upper limit of the normal reference range was 27 mg/dL for BUN and 1.8 mg/dL for creatinine. For felines, the upper limit of the normal reference range was 34 mg/dL for BUN, and 2.3 mg/dL for creatinine.

The results in Table 3 show that SDMA levels were elevated in dogs and cats with compromised kidney function. Thus, SDMA can be used as a marker to diagnose renal disease in animals.

Example 6

Analysis of Canine Glomerular Filtration Rate with Creatinine Concentration and Free SDMA Concentration Serum samples were taken from heterozygous (carrier) female dogs (n=20) with X-linked hereditary neuropathy (XLHN). XLHN is caused by a mutation in the gene COL4A5, which in the female dogs causes a mosaic expression of type IV collagen peptides and onset of glomerular proteinuria between 3 and 6 months of age. (Nabity et al., J Vet Intern Med 2007; 21:425-430) Concentrations of creatinine and SDMA were measured in each sample.

The creatinine concentration of the samples was measured using IDEXX dry-slide technology as described above.

The free SDMA concentrations of the samples were determined as follows: The LCMS mobile phases were (A) 10 mL propionic acid and 250 µL of trifluoroacetic acid in 1 L of water; and (B) 10 mL propionic acid and 250 µL of trifluoroacetic acid in 1 L acetonitrile An internal standard of 2.5 ng/mL deuterated asymmetric dimethyl arginine (d-ADMA) in water was prepared. The STD (standard) curve was made in stripped canine serum by spiking 20 µg/mL of SDMA solution, followed by dilutions to get a 9-point STD curve varying in concentrations from 1.56 µg/dL to 100 µg/dL. To perform the measurements, 100 µL of the sample to be measured (i.e., a serum sample or a standard solution) were transferred into microfuge tubes. 10 µL of the internal standard solution and 200 µL of mobile phase B were added to each tube. The tubes were vortexed to mix and allowed to sit for 30 min, then centrifuged at 13000 g for 20 minutes at 25° C. The supernatants were transferred into 2 mL amber HPLC vials, and the samples analyzed by LCMS. The LCMS was performed on HPLC and API-4000 from ABSciex, run with scan type MRM, positive polarity, turbo spray scan mode, Q1 resolution=unit and Q3 resolution=unit. The column was a 150×4.6 PVA SIL column, flow was 1 mL/min and the gradient was isocratic 90:10 B:A. The chromatograms were run for 9 min at ambient temperature.

The actual GFR of the animals were measured by the iohexol clearance method. Subjects were injected with iohexol.

Blood samples were taken at various time intervals, and serum iohexol was measured by HPLC.

Figure 5:
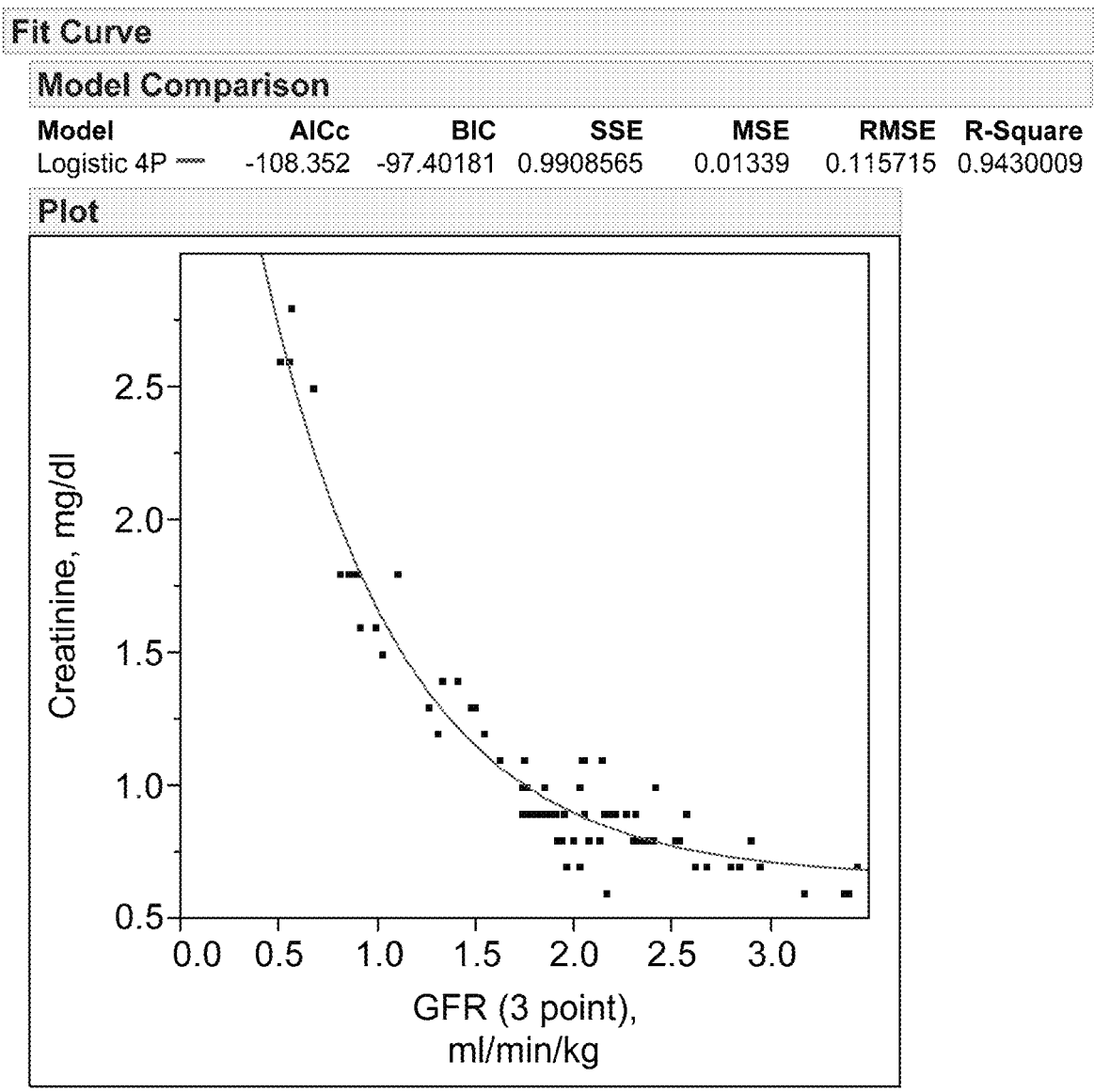
FIG. 5 is a plot of creatinine concentration vs. GFR for a set of canine serum samples, as described in Example 6.

Three data points were collected for each dog. A four parameter logistic (4PL) plot of creatinine concentration (mg/dL) vs. GFR (ml/min/kg) is provided in FIG. 5. The value of $R^2$ for these data is 0.94 with a standard error of 0.12 over a 0.5-3.0 mg/dl concentration range, which represents roughly 5% of the total range.

Figure 6:
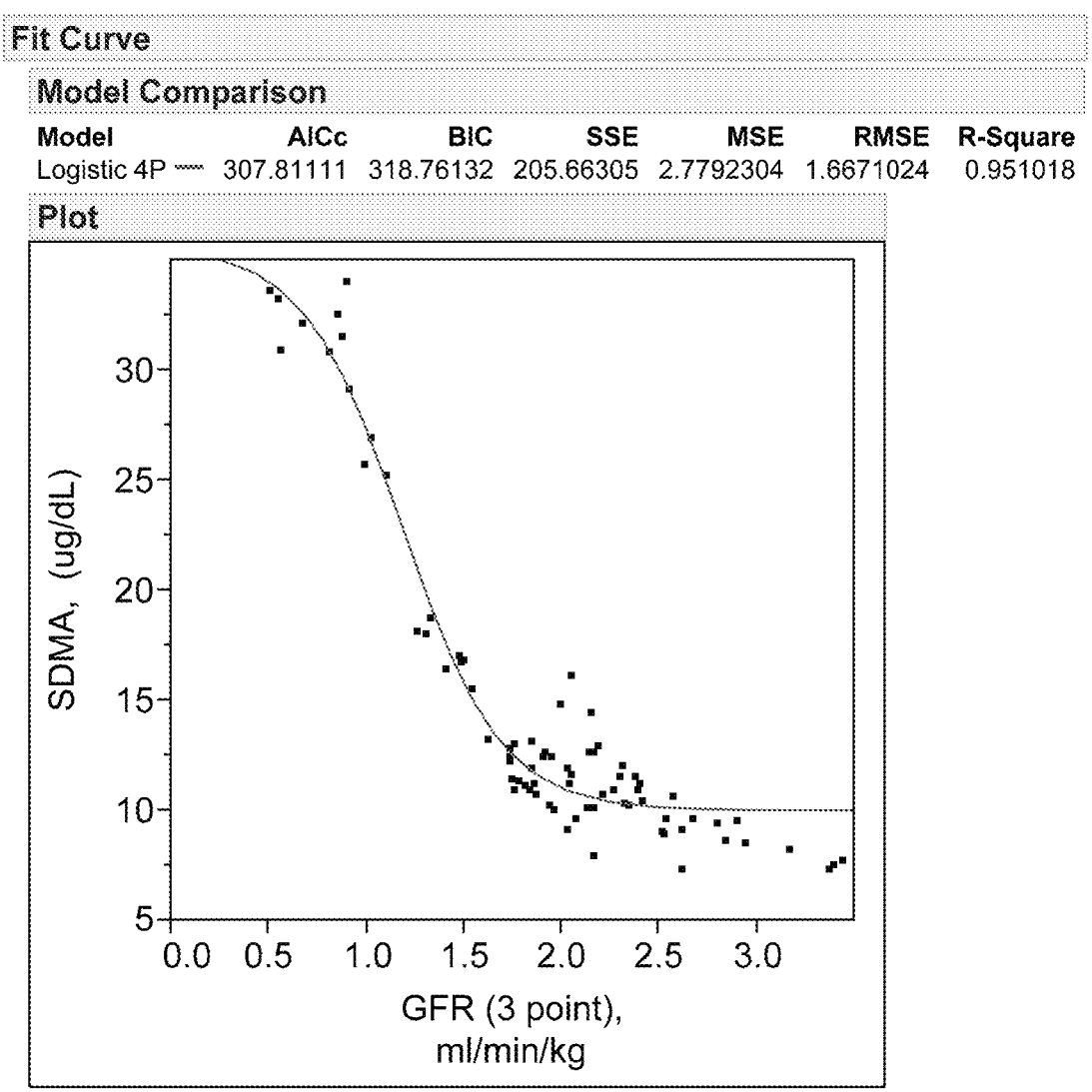
FIG. 6 is a plot of SDMA concentration vs. GFR for a set of canine serum samples, as described in Example 6.

FIG. 6 shows the results of SDMA concentration (µg/dl) vs. GFR (ml/min/kg). 4A PL fit to the SDMA-GFR relationship provides an $R^2$ value of 0.95, with a standard error of 1.7 over a 5-40 µg/dL range for SDMA. This error represents roughly 5% of the total range.

FIG. 7 shows the results of combining creatinine values and SDMA values using simple multiplication of the values, which shows an improvement to the relationship to GFR over creatinine alone or SDMA alone. The 4PL fit of the [Creatinine]*[SDMA]–GFR relationship provides an $R^2$ value of 0.98, with a standard error of 2.8 over a 0-90 µg/dL range for [Creatinine]*[SDMA]. This error represents roughly 3% of the total range to the relationship to GFR for these dogs.

Figure 8:
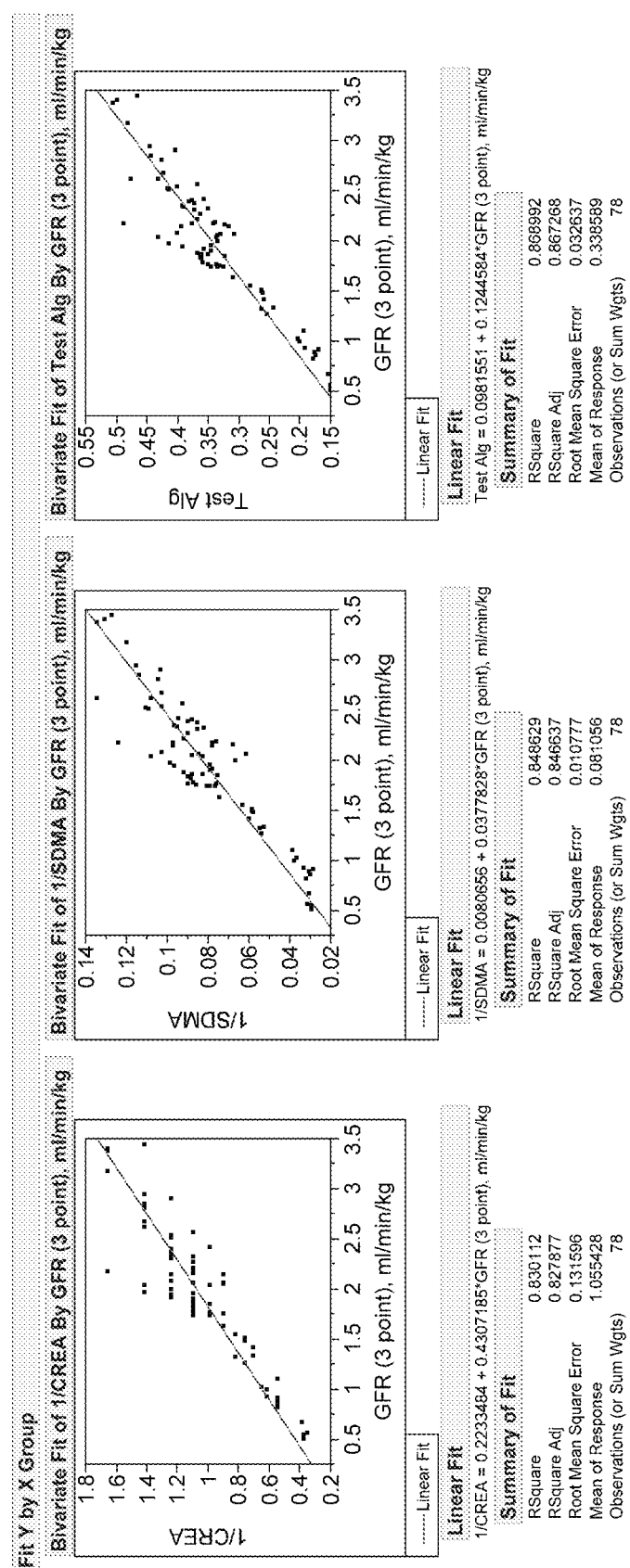
FIG. 8 shows plots, using a linear fit, of creatinine vs. GFR, 1/SDMA vs. CGF and $1/[Creatinine^{0.37}]*1/[SDMA^{0.43}]$ vs. Creatinine for a set of canine serum samples, as described in Example 6.

FIG. 8 shows the analysis of $1/[\text{Creatinine}]^P * 1/[\text{SDMA}]^Q$, using linear fit. Using linear regression, P was 0.37 and Q was 0.43. The $R^2$ for the combination yielded a value of 0.87, as compared to 0.83 for 1/[Creatinine] alone and 0.85 for 1/[SDMA] alone.

Example 7

Analysis of Feline Glomerular Filtration Rate with Creatinine Concentration and Free SDMA Concentration Ten female cats with 1 to 4 data points each were used to evaluate whether the multiplicative combination of SDMA and creatinine values were better correlated to GFR than the individual marker values alone. SDMA, creatinine and GFR were measured as described above.

Figure 9:
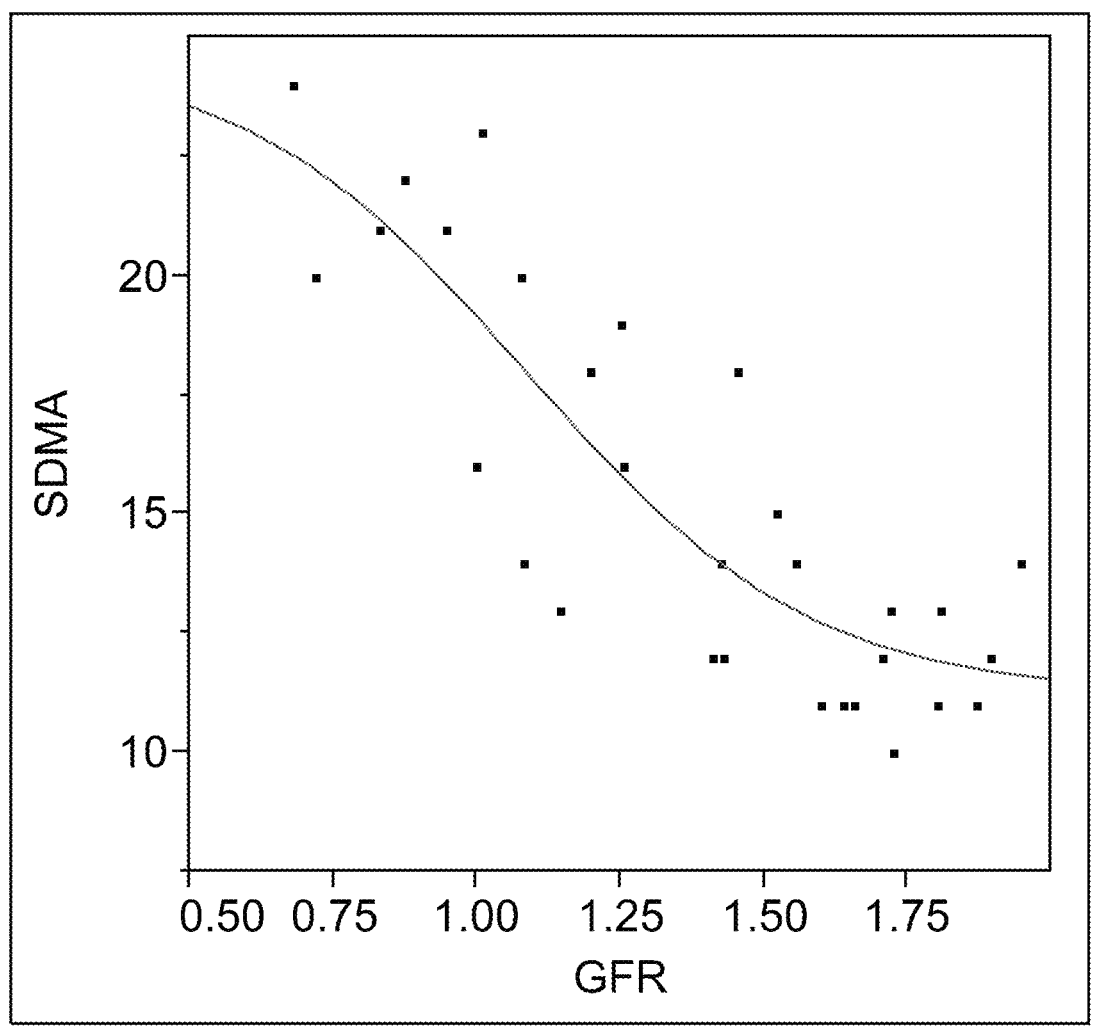
FIG. 9 is a plot of SDMA concentration vs. GFR for a set of feline serum samples, as described in Example 7.

FIG. 9 shows the results of SDMA concentration (µg/dl) vs. GFR (ml/min/kg). A 4 PL fit to the SDMA-GFR relationship provides an $R^2$ value of 0.73, with a standard error of 2.3 over a 15 µg/dL range for SDMA. This error represents roughly 15% of the total range.

Figure 10:
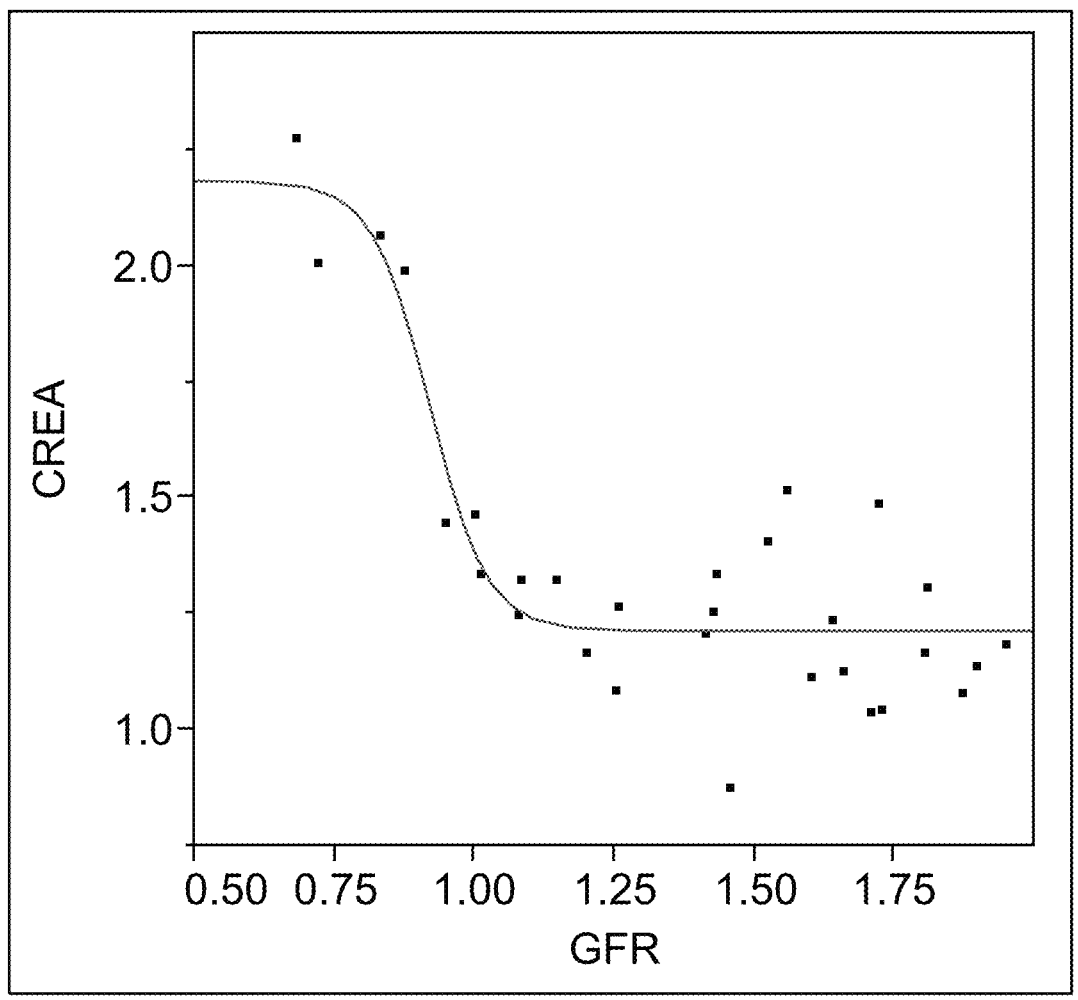
FIG. 10 is a plot of creatinine concentration vs. GFR for a set of feline serum samples, as described in Example 7.

FIG. 10 shows the results of creatinine concentration (mg/dl) vs. GFR (ml/min/kg). A 4 PL fit to the Creatinine-GFR relationship provides an $R^2$ value of 0.82, with a standard error of 0.15 over a 1.5 mg/dL range. This error represents roughly 10% of the total range.

Figure 11:
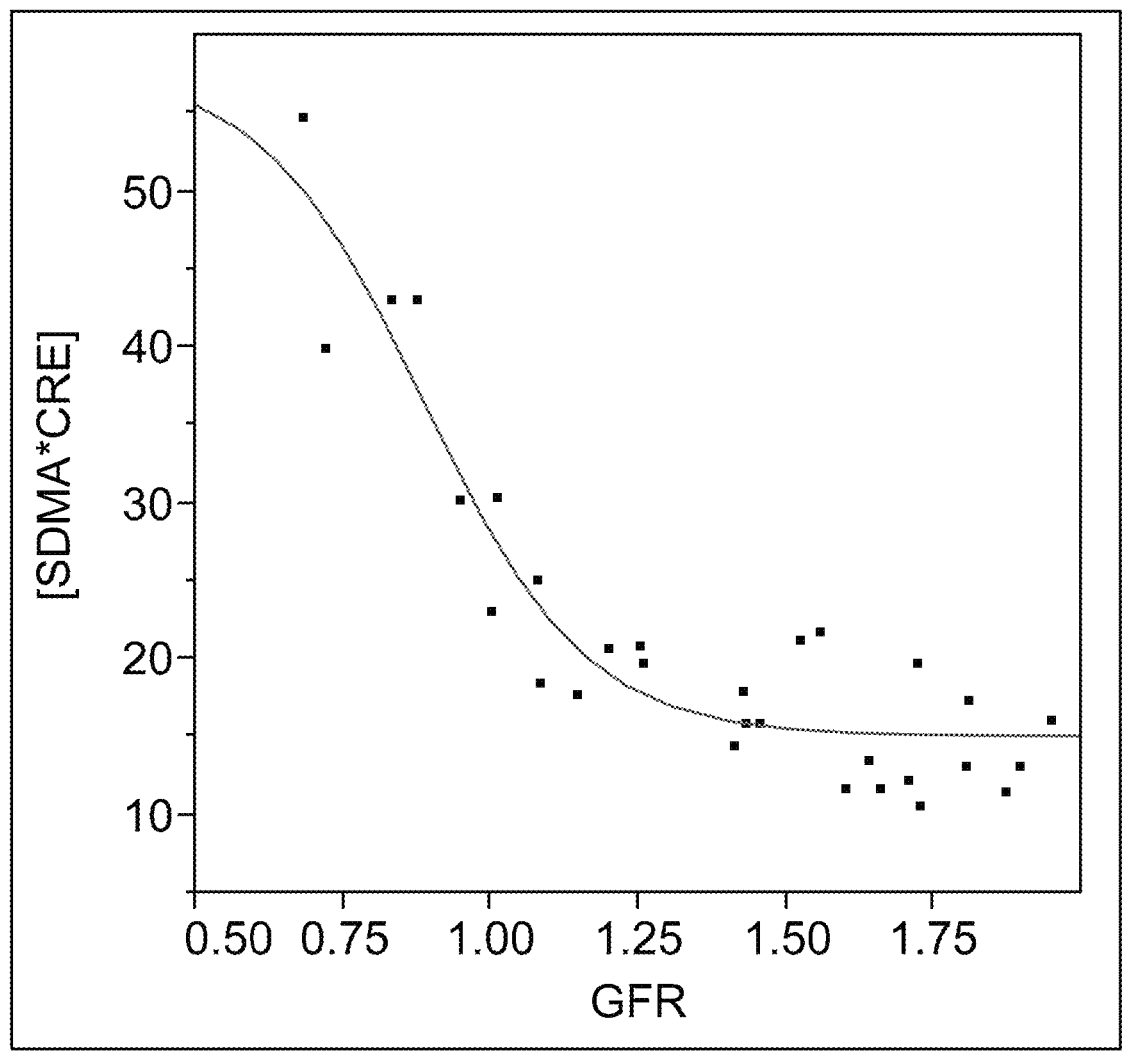
FIG. 11 is a plot of [Creatinine]*[SDMA] vs. GFR for a set of feline serum samples, as described in Example 7.

FIG. 11 shows the results of combining creatinine values and SDMA values using simple multiplication of the values, which shows an improvement to the relationship to GFR over creatinine alone or SDMA alone. The 4PL fit of the [Creatinine]*[SDMA]–GFR relationship provides an $R^2$ value of 0.89, with a standard error of 3.9 over a 40 µg/dL range for [Creatinine]*[SDMA]. This error represents roughly 10% of the total range.

Figure 12:
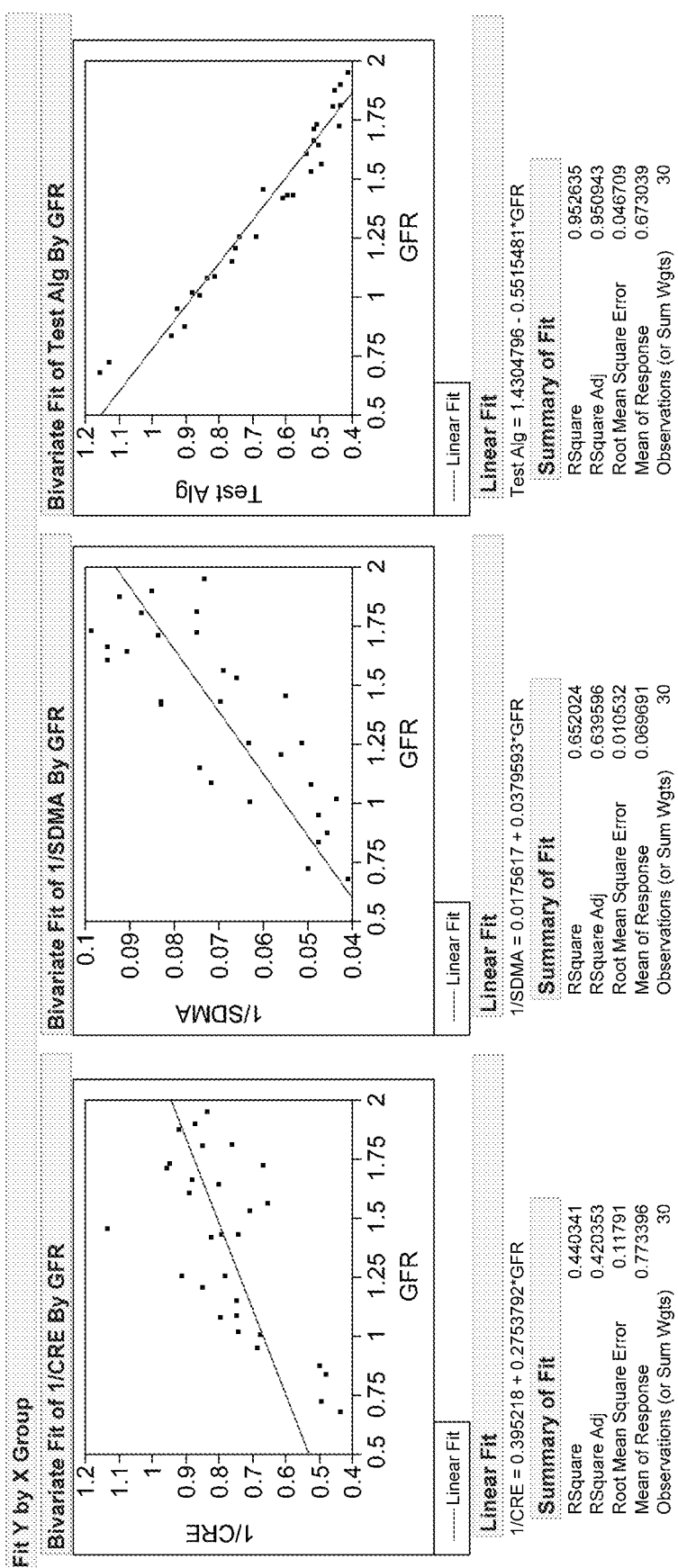
FIG. 12 shows plots, using a liner fit, of [Creatinine] vs. GFR, 1/SDMA vs. CGF, and $1/[Creatinine^{1.2}]*1/[SDMA^{0.39}]$ vs. creatinine for a set of canine serum samples, as described in Example 7.

FIG. 12 shows the analysis of $1/[\text{Creatinine}]^P * 1/[\text{SDMA}]^Q$, using linear fit. Using linear regression, P was 1.2 and Q was 0.95. The $R^2$ for the combination yielded a value of 0.95, as compared to 0.44 for 1/[Creatinine] alone and 0.65 for 1/[SDMA] alone.

Example 8

Improving the Sensitivity and/or Specificity in the Diagnosis of Renal Disease Through a Combination of CRE and SDMA Cutoff Values The kidney disease status of 113 cats was determined and staged according to the Algorithm for Staging of Chronic Kidney Disease (CKD) in dogs and cats as provided by the International Renal Interest Society (IRIS). For each cat, 1 to 6 serum samples taken at various time points were analyzed for creatinine [CRE] and/or SDMA. 194 samples came from 61 normal cats (i.e., no CKD). 182 samples came from 55 cats suffering from CKD.

In this Example, cut off values for SDMA and CRE were determined and used to determine CKD. The cutoff value represents the threshold serum concentration above which the individual is diagnosed as having renal disease for this particular test. $SDMA_{CUT}$ is the cutoff value for SDMA. [SDMA] and $SDMA_{CUT}$ are measured in µg/dL (micrograms/deciliter). For example, $SDMA_{CUT}$ may be about 14 µg/dL, or between about 10 and 20 µg/dL.

$CRE_{CUT}$ is the cutoff value for CRE. CRE and $CRE_{CUT}$ are measured in mg/dL. For example, $CRE_{CUT}$ may be from about 2.0 mg/dL to 2.4 mg/dL, or between about 1.7 and 2.8 mg/dL.

For SDMA alone, a cut off value ($SDMA_{CUT}$) was set at 14 µg/dL. Using this value, there were 10.3% false positive rate for normal cats, and a 26.9% false negative rate for CKD cats (see Table 4).

TABLE 4

| | % False positives | # False positives | % False negatives | # False negatives | % Positive Diagnosis | # Total |
|---|---|---|---|---|---|---|
| Normal | 10.3 | 20 | | | 89.7 | 194 |
| KD | | | 26.9 | 49 | 73.1 | 182 |

For creatinine alone, a cut-off value ($CRE_{CUT}$) was set at 2.4 mg/dL. Using this value, there were 0.0% false positive rate for normal cats, and a 43.4% false negative rate for CKD cats (see Table 5).

TABLE 5

| | % False positives | # False positives | % False negatives | # False negatives | % Positive Diagnosis | # Total |
|---|---|---|---|---|---|---|
| Normal | 0.0 | 0 | | | 100.0 | 194 |
| KD | | | 43.4 | 79 | 56.6 | 182 |

$C_{CUT}$ is the cutoff value for the Combination Value C. Creatinine and SDMA values were combined according to the formula:

Combination Value $C=[SDMA]/SDMA_{CUT}+[CRE]/CRE_{CUT}$.

$C_{CUT}$ does not have a unit of measurement. For example, $C_{CUT}$ may be 1.5, 1.7 or 2.0, or between 1.3 and 2.5.

When $C_{CUT}$ was set at 1.5, there was a 12.4% false positive rate for normal cats, and a 1.6% false negative rate for CKD cats (see Table 6). When $C_{CUT}$ was set at 1.7, there was a 3.5% false positive rate for normal cats, and a 14.3% false negative rate for CKD cats (see Table 7). When $C_{CUT}$ was set at 2.0, there was a 3.5% false positive rate for normal cats, and a 33.5% false negative rate for CKD cats (see Table 8).

TABLE 6

| | % False positives | # False positives | % False negatives | # False negatives | % Positive Diagnosis | # Total |
|---|---|---|---|---|---|---|
| Normal | 12.4 | 25 | | | 87.6 | 194 |
| KD | | | 1.6 | 3 | 98.4 | 182 |

TABLE 7

| | % False positives | # False positives | % False negatives | # False negatives | % Positive Diagnosis | # Total |
|---|---|---|---|---|---|---|
| Normal | 3.5 | 7 | | | 96.5 | 194 |
| KD | | | 14.3 | 26 | 85.7 | 182 |

TABLE 8

| | % False positives | # False positives | % False negatives | # False negatives | % Positive Diagnosis | # Total |
|---|---|---|---|---|---|---|
| Normal | 3.5 | 7 | | | 96.5 | 194 |
| KD | | | 33.5 | 61 | 66.5 | 182 |

The estimated sensitivity and specificity of the Combination Value was plotted against $C_{CUT}$ to determine suitable values for $C_{CUT}$ (see FIG. 13). If C is greater than (>) $C_{CUT}$, the individual is diagnosed as having kidney disease. Accordingly, combining SDMA and CRE values based on their respective diagnostic cutoff values leads to improved sensitivity and/or specificity of detection of kidney disease in animals.

Example 9

Determination of Ratio of Creatinine to SDMA in Healthy and Diseased Animals

In healthy animals, the ratio of the concentration of SDMA (µg/dL) and creatinine (mg/dL) ranges generally from about 4:1 to 10:1 (µg/dL:mg/dL). In some chronic kidney disease patients, this ratio exceeds 10:1, which can indicate the progression of disease.

In this study, longitudinal trending of SDMA and creatinine in CKD dogs was observed. Twenty four dogs with CKD were included in the study based on the following criteria: Age (9.4-18.3 y); persistently azotemic (>3 months); GFR; physical examination; serum creatinine, and urinalysis.

All dogs were maintained with quality care including optimal nutrition, veterinary healthcare, and daily exercise. After diagnosis with CKD, the dogs were fed PRESCRIPTION DIET® k/d® dog food (Hill's Pet Nutrition, Inc., Topeka, Kans.).

Samples were collected from these dogs on a regular basis (2-3 times a year). Samples were frozen and banked. creatinine was measured by enzymatic colorimetry using the COBAS® analyzer. SDMA was measured by LCMS as described above with the exception that serum samples were precipitated with acetonitrile, and that a Waters XBridge C18 5 µm 4.6*30 column was used. Mobile phase A consisted of 0.5 mM perflorohepatonic acid in 0.1% formic acid in water and mobile phase B is 0.1% formic acid in acetonitrile with a gradient of 100% B to 100% A with run time of 4 minutes. The correlation between SDMA (µg/dL) and creatinine (mg/dL) is shown in FIG. 14.

Example 10

Discordance Between SDMA and Creatinine Values in Some Cats with CKD

Discordance in the SDMA:creatinine ratio may be predictive of mortality in animals. For instance, in CKD cats, the observed SDMA values were high relative to the expected concentrations based upon corresponding creatinine values. As shown in FIG. 14, there is strong correlation between SDMA and creatinine, and the normal ratio is less than 10 (µg/dL:mg/dL). In this study, the ratio was determined in 26 CKD cats. These 26 cats had been diagnosed with CKD based on physical exam, serum creatinine, and urinalysis. As shown in FIG. 15, two out of the 26 cats had a SDMA:creatinine ratio of greater than 10 and had died at the time of follow-up, although it was not documented whether these cats were euthanized or succumbed to disease.

Example 11

SDMA: Creatinine Ratio in the Prediction of Mortality in Cats with CKD

In this study, longitudinal trending of SDMA and creatinine in CKD cats was observed. Eighteen cats with CKD were included in the study based on the following criteria: persistently azotemic for at least 3 months; or nonazotemic with a >30% reduction in GFR from median GFR of normal cats; or calcium oxalate kidney stones.

All cats were maintained with quality care including optimal nutrition, veterinary healthcare, and daily exercise, and regular opportunities for environmental and behavioral enrichment. After diagnosis with CKD, the cats were fed PRESCRIPTION DIET® c/d® food (Hill's Pet Nutrition, Inc., Topeka, Kans.).

Blood and urine samples from these cats were collected at various times, frozen and banked. Creatinine was measured by enzymatic colorimetry using the COBAS® analyzer. SDMA was measured by LCMS as described above.

At the time the concentration of SDMA first reached or exceeded 14 µg/dL in each of the 18 cats, 12 cats had an SDMA:creatinine ratio of greater than 10:1, and 6 cats had an SDMA:creatinine ratio that was 10:1 or less. For each cat, the time from the date the concentration of SDMA first reached or exceeded 14 µg/dL until the date of death was observed, with the exception of two cats. These two cats were still alive at the conclusion of the study; thus, the end date of the study was substituted for the date of death for these two cats.

The 12 cats that had an SDMA:creatinine ratio of greater than 10:1, had a median survival time of 13.9 months (mean=18.7; range=1.8-47.4). The 6 cats that had an SDMA:creatinine ratio of 10:1 or less had a median survival time of 18.7 months (mean=18.9; range=8.7-28.7). Thus, the cats that had an SDMA:creatinine ratios of greater than 10:1, had a higher mortality than the cats that had an SDMA: creatinine ratios of 10:1. FIGS. 16, 17 and 18 show the time course of SDMA:creatinine ratios for three cats from the study, with SDMA:creatinine ratios exceeding 10 (cat #13, cat #8 and cat #14), over the course of several years. Cat #13 died at 27.2 months, Cat #8 died at 29.4 months, and cat #14 died at 12.3 months, after the date the serum SDMA concentration first reached at least 14 µg/dL. At the last measurement on necropsy, the ratios for the three cats ranged from approximately 17 to 34.

Example 12

Prediction of Mortality Using SDMA and Creatinine

FIGS. 19 and 20 shows a Kaplan-Meier survival curve for cats (from the study described in Example 11) and dogs (from the study described in Example 9) using an SDMA cut-off value of 14 µg/dL. FIG. 19 shows that cats having a SDMA serum concentration of at least 14 µg/dL had reduced survival time and increased chance of mortality. Cats with serum SDMA less than 14 µg/dL survived approximately 1.6 times longer than cats having serum SDMA equal to or greater than 14 µg/dL. In this study, creatinine failed to predict mortality in cats (2.1 mg/dL reference cut off).

FIG. 20 shows that a Kaplan-Meier survival curve for dogs having serum SDMA concentration greater or less than 14 µg/dL. In this study, dogs with SDMA <14 µg/dL survived 2.6 times longer compared to dogs with SDMA ≥14 µg/dL. Creatinine failed to predict mortality (1.5 mg/dL reference cut-off).

The examples given above are merely illustrative and are not meant to be an exhaustive list of all possible embodiments, applications or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to the skilled artisan.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. It also is to be noted that, as used herein and in the appended claims, the singular forms "a," "an," and "the" include the plural reference unless the context clearly dictates otherwise. Thus, for example, a reference to "a linker" is a reference to one or more linkers and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Particular methods, devices, and materials are described, although any methods and materials similar or equivalent to those described herein can be used in the practice or testing of the invention. The disclosures of all references and publications cited above are expressly incorporated by reference in their entireties to the same extent as if each were incorporated by reference individually.

What is claimed is:

1. A method of determining whether a canine or feline subject has kidney disease, the method comprising:
   (a) measuring concentrations of free symmetrical dimethylarginine (SDMA) [SDMA] and creatinine [CRE] in a serum sample from the canine or feline subject, wherein measuring free [SDMA] comprises:
      contacting the sample with an anti-SDMA antibody, wherein the antibody is specific for free SDMA; and
      detecting complexes of the anti-SDMA antibody and SDMA;
   (b) calculating a Combination Value: $C=[SDMA]/SDMA_{CUT}+[CRE]/CRE_{CUT}$, wherein $SDMA_{CUT}$ is the cutoff value for [SDMA], $CRE_{CUT}$ is the cutoff value for [CRE],
   (c) determining a cutoff value ($C_{CUT}$) for the combination value to accommodate a desired level of specificity and/or sensitivity for the detection of kidney disease, and
   (d) determining that the canine or feline subject has kidney disease if C is greater than $C_{CUT}$.

2. The method of claim 1, wherein the $SDMA_{CUT}$ is between 10 and 20 µg/dL.

3. The method of claim 1, wherein the $CRE_{CUT}$ is between 1.3 to 2.5 mg/dL.

4. The method of claim 1, wherein the $CRE_{CUT}$ is between 1.7 to 2.8 mg/dL.

5. The method of claim 1, wherein $C_{CUT}$ is between 1.3 and 2.5.

6. The method of claim 1, wherein the anti-SDMA antibody has no or substantially no cross-reactivity with one or more compounds selected from the group consisting of asymmetrical dimethylarginine (ADMA), L-arginine, and N-methylarginine.

7. The method of claim 6, wherein the anti-SDMA antibody has reactivity for ADMA of less than 25% of its reactivity for SDMA.

8. The method of claim 6, wherein the anti-SDMA antibody has reactivity for ADMA of less than 10% of its reactivity for SDMA.

9. The method of claim 6, wherein the anti-SDMA antibody has reactivity for ADMA of less than 5% of its reactivity for SDMA.

10. The method of claim 6, wherein the anti-SDMA antibody has reactivity for ADMA of less than 1% of its reactivity for SDMA.

* * * * *

UNITED STATES PATENT AND TRADEMARK OFFICE
CERTIFICATE OF CORRECTION

Page 1 of 1

PATENT NO.         : 11,035,861 B2
APPLICATION NO.    : 15/061327
DATED              : June 15, 2021
INVENTOR(S)        : M. Yerramilli et al.

It is certified that error appears in the above-identified patent and that said Letters Patent is hereby corrected as shown below:

In the Claims

Claim 1, Column 39, Line 13, please replace "C = [SDMA] / $SDMA_{CUT\,+}$ [CRE] / $CRE_{CUT}$," with --C = [SDMA] / $SDMA_{CUT}$ + [CRE] / $CRE_{CUT}$,--

Signed and Sealed this
Twenty-ninth Day of March, 2022

Drew Hirshfeld
*Performing the Functions and Duties of the
Under Secretary of Commerce for Intellectual Property and
Director of the United States Patent and Trademark Office*